(12) United States Patent
Baker et al.

(10) Patent No.: US 8,501,995 B2
(45) Date of Patent: Aug. 6, 2013

(54) β-PHENYLETHYLIDENEHYDRAZINE DERIVATIVES

(75) Inventors: Glen Baker, Edmonton (CA); Edward Knaus, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 272 days.

(21) Appl. No.: 12/833,453

(22) Filed: Jul. 9, 2010

(65) Prior Publication Data

US 2011/0009492 A1 Jan. 13, 2011

Related U.S. Application Data

(60) Provisional application No. 61/224,499, filed on Jul. 10, 2009.

(30) Foreign Application Priority Data

Jul. 10, 2009 (CA) ..................................... 2671320

(51) Int. Cl.
*C07C 243/16* (2006.01)

(52) U.S. Cl.
USPC ............ 564/248; 564/251; 514/565; 514/639

(58) Field of Classification Search
USPC .......... 514/639, 318, 149, 426, 565; 564/251, 564/248
See application file for complete search history.

(56) References Cited

U.S. PATENT DOCUMENTS

| 3,083,229 A | 3/1963 | Oja | |
|---|---|---|---|
| 2005/0080260 A1* | 4/2005 | Mills et al. | 544/237 |
| 2006/0089335 A1* | 4/2006 | Liu et al. | 514/114 |

OTHER PUBLICATIONS

MacKenzie et al; Bioorganic and Medicinal Chemistry, 16 (2008), 8254-8263.*
Paslawski et al; Drug Development Research, 54, 35-39 (2001).*
Sowa et al; Bioorganic and Medicinal Chemistry, 13 (2005) 4389-4395.*
Am, et al. Neurosci Lett. 2004, 355, 169-172.
Bach, et al. Xenobiotica. 2000, 30, 297-306.
Baker, et al. J Affect Disord. 1991, 21, 207-211.
Brown, et al. J Am Chem Soc. 1966, 88, 1458-&.
Cameron, et al. Aust J Chem. 1982, 35, 1469-1480.
Coyle, Cell Mol Neurobiol. 2006, 26, 365-384.
Curtis, et al. Exp Brain Res. 1968, 5, 235-258.
Emilsson, et al. Neurosci Lett. 2002, 326, 56-60.
Grant, et al. J Chromatogr B Analyt Technol Biomed Life Sci. 2006, 844, 278-282.
Heinonen, et al. Acta Neurol Scand Suppl. 1989, 126, 93-99.
Javitt, Biol Psychiatry. 2008, 63, 6-8.
Kalasz, et al. J Chromatogr. 1990, 499, 589-599.
Karabats, et al. Tetrahedron. 1968, 24, 3361-&.
Li, et al. Synthetic Commun. 1995, 25, 533-537.
Ling, et al. Bioorg Med Chem Lett. 2001, 11, 2715-2717.
Lyles, et al. Biochem Pharmacol. 1982, 31, 1417-1424.
MacKenzie, et al. Neurochem Res. 2008, 33, 430-436.
McKenna, et al. Naunyn Schmiedeberg's Arch Pharmacol. 1991, 343, 478-482.
McManus, et al. Biochem Pharmacol. 1992, 43, 2486-2489.
Michael-Titus, et al. Neuroscience. 2000, 100, 681-684.
Olsen, et al. In Basic Neurochemistry: Molecular, Cellular and Medicinal Aspects; G. J. Siegel, R. W. Albers, S. T. Brady and D. L. Price, Ed.; Academic Press: New York, N.Y., 2006; pp. 291-301.
Parent, et al. Biochem Pharmacol. 2000, 59, 1253-1263.
Parent, et al. Psychopharmacology (Berl). 1999, 142, 280-288.
Parent, et al. Biochem Pharmacol. 2002, 63, 57-64.
Paslawski, et al. Prog Brain Res. 1995, 106, 181-186.
Paslawski, et al. Drug Devel Res. 2001, 54, 35-39.
Paslawski, et al. Psychopharmacology (Berl). 1996, 127, 19-24.
Patek, et al. J Biol Chem. 1974, 249, 2373-2380.
Philips, J Pharm Pharmacol. 1981, 33, 739-741.
Pirisino, et al. Br J Clin Pharmacol. 1978, 7, 595-598.
Popov, et al. J Neurochem. 1969, 16, 899-907.
Rao, et al. Brain Res Bull. 1987, 19, 47-55.
Rao, et al. Naunyn Schmiedebergs Arch Pharmacol. 1987, 336, 25-32.
Ratcliffe, et al. J Org Chem. 1970, 35, 4000-&.
Reynolds, et al. J Neural Transm. 1978, 43, 271-277.
Rittenbach, et al. Cell Mol Neurobiol. 2007, 27, 179-190.
Sethi, J Pharm Biomed Anal. 1993, 11, 613-617.
Shin, Drug Metab Dispos. 1997, 25, 657-662.
Sterri, et al. Eur J Biochem. 1978, 91, 215-222.
Tanay, et al. Int J Neuropsychopharmacol. 2002, 5, S94.
Tipton, Biochem J. 1972, 128, 913-919.
Tipton, et al. Biochem Pharmacol. 1972, 21, 268-270.
Todd, etal. J Affect Disord. 1995, 35, 125-129.
Weli, et al. Biochem Pharmacol. 1985, 34, 1993-1998.
Weli, et al. Xenobiotica. 1986, 16, 281-288.
Wood, et al. Brain Res. 2006, 1122, 184-190.
Yang, et al. Neuroscience. 2005, 135, 927-937.
Yoshida, et al. Xenobiotica. 1986, 16, 129-136.
Yu, et al., Biochem Pharmacol. 1989, 38, 4245-4251.

* cited by examiner

*Primary Examiner* — Johann R Richter
*Assistant Examiner* — Pancham Bakshi
(74) *Attorney, Agent, or Firm* — Choate, Hall & Stewart, LLP; Andrea L. C. Robidoux; Xiaodong Li

(57) ABSTRACT

The present invention provides new β-phenylethylidenehydrazine derivatives, processes for preparing them and their use as pharmaceutical compostions. The β-phenylethylidenehydrazine derivatives according to the invention generally correspond to the general formula:

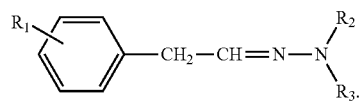

15 Claims, 5 Drawing Sheets

β-PHENYLETHYLIDENEHYDRAZINE DERIVATIVES

FIELD OF THE INVENTION

The field of the invention generally relates to novel compounds, pharmaceutical compositions containing said compounds and their therapeutic use.

BACKGROUND OF THE INVENTION

β-Phenylethylidenehydrazine [PEH; FIG. 1(1)] is a metabolite of the antidepressant/antipanic/neuroprotective drug phenelzine [PLZ; FIG. 1(2)] and is thought to be formed by the action of monoamine oxidase (MAO) on PLZ.[1-4]

PEH shares a number of neurochemical properties with PLZ, including (a) the inhibition of GABA-transaminase (GABA-T) activity;[5] (b) the ability to increase brain levels of GABA,[5,6] alanine and ornithine;[7] and (c) the ability to transiently decrease brain levels of glutamine.[5] Inhibition of MAO prior to PLZ administration, prevents some of these effects, such as inhibition of GABA-T, and elevation of GABA and ornithine.[8-10]

PEH formation may also contribute to some of the therapeutic effects of PLZ. For example, the anxiolytic properties of PLZ have been shown to be related to the drug's facilitatory effect on GABAergic transmission,[11] and given that the increase in GABA appears to be dependent upon PEH formation, it is reasonable to suggest that PEH may mediate the anxiolytic effects of PLZ. Furthermore, PLZ and PEH have been shown to be neuroprotective in animal models of global ischemia,[12,13] and while the mechanism(s) for this have not been elucidated, the ability of PLZ to reduce glutamatergic transmission,[14,15] the ability of PLZ to sequester reactive aldehydes,[12] and the ability of both drugs to increase brain GABA[8,16-21] may contribute to neuroprotection. PEH differs from PLZ in that it does not appreciably inhibit MAO activity.[5]

Given the strict dietary restrictions that are necessary for individuals taking PLZ due to potentially dangerous interactions between the drug and tyramine-rich foods, PEH may be a useful alternative for conditions thought to involve GABAergic dysfunction and in which PLZ is effective (e.g. depression, social anxiety disorder, panic disorder) but is not used as a first-line drug because of this adverse effect.

There remains a need for improved PEH analogues.

This background information is provided for the purpose of making known information believed by the Applicant to be of possible relevance to the present invention. No admission is necessarily intended, nor should be construed, that any of the preceding information constitutes prior art against the present invention.

SUMMARY OF THE INVENTION

In accordance with one aspect of the present invention, there is provided a compound having the formula (I), or a pharmaceutically acceptable salt thereof:

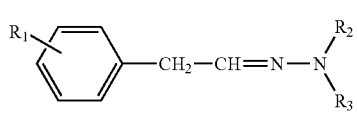

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$. In a specific aspect, $R_1$ is H, $R_2$ is $CH_2CCH$ and $R_3$ is $CH_2CCH$ (7p in FIG. 2). In another specific aspect, $R_1$ is H, $R_2$ is H and $R_3$ is $CH_2CCH$ (8p in Figure).

In accordance with another aspect of the present invention, there is provided a method of treating a subject suffering from schizophrenia comprising, administering to said subject an effective amount of a compound having the formula (I):

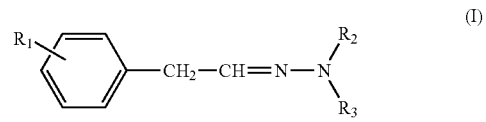

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; or pharmaceutically acceptable salt of said compound. In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

In accordance with another aspect of the present invention, there is provided a method of increasing glycine levels in the brain of a subject, comprising administering to said subject an effective amount of a compound having the formula (I):

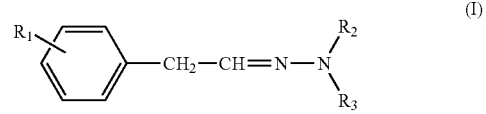

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; or pharmaceutically acceptable salt of said compound In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

In accordance with another aspect of the present invention, there is provided a use of a compound having the formula (I), or a pharmaceutically acceptable salt thereof:

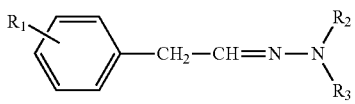

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; in the manufacture of a medicament to treat a subject having schizophrenia. In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

In accordance with another aspect of the present invention, there is provided a use of a compound having the formula (I), or a pharmaceutically acceptable salt thereof:

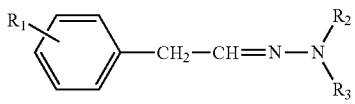

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; in the manufacture of a medicament increasing glycine levels in the brain of a subject. In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

In accordance with another aspect of the present invention, there is provided a a pharmaceutical composition comprising a therapeutically effective amount of a compound having the formula (I), or a pharmaceutically acceptable salt thereof:

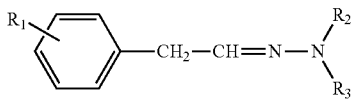

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; and a pharmaceutically acceptable carrier. In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

In accordance with another aspect of the present invention, there is provided a kit comprising: a compound having the formula (I), or a pharmaceutically acceptable salt thereof:

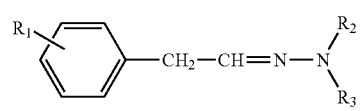

wherein $R_1$ is H, $R_2$ is $CH_2CCH$ and $R_3$ is $CH_2CCH$; $R_1$ is H, $R_2$ is H and $R_3$ is $CH_2CCH$; R1 is $CH_3$, $R_2$ is H and $R_3$ is $CH_2CCH$; R1 is $OCH_3$, $R_2$ is H and $R_3$ is $CH_2CCH$; $R_1$ is Cl, $R_2$ is H and $R_3$ is $CH_2CCH$; $R_1$ is F, $R_2$ is H and $R_3$ is $CH_2CCH$; $R_1$ is $CF_3$, $R_2$ is H and $R_3$ is $CH_2CCH$; $R_1$ is $CH_3$, $R_2$ is $CH_2CCH$ and $R_3$ is $CH_2CCH$; $R_1$ is $OCH_3$, $R_2$ is $CH_2CCH$ and $R_3$ is $CH_2CCH$; $R_1$ is Cl, $R_2$ is $CH_2CCH$ and $R_3$ is $CH_2CCH$; $R_1$ is F, $R_2$ is $CH_2CCH$ and $R_3$ is $CH_2CCH$; or $R_1$ is $CF_3$, $R_2$ is $CH_2CCH$ and $R_3$ is $CH_2CCH$; and b. instructions for the use thereof. In a specific aspect, $R_1$ is H, $R_2$ is $CH_2CCH$ and $R_3$ is $CH_2CCH$. In another specific aspect, $R_1$ is H, $R_2$ is H and $R_3$ is $CH_2CCH$.

BRIEF DESCRIPTION OF THE DRAWINGS

Embodiments of the present invention will now be described, by way of example only, with reference to the attached Figures, wherein:

FIG. 1(1)) and phenelzine (PLZ; FIG. 1(2));

DETAILED DESCRIPTION

As will be described in more detail below, the present invention relates to novel compounds, pharmaceutical compositions containing said compounds and their therapeutic use.

As described herein, a group of β-phenylethylidenehydrazines possessing a variety of substituents (H, Me, OMe, Cl, F, $CF_3$) at the ortho-, meta- or para-positions of the phenyl ring, in conjunction with either a N-bis-(2-propynyl) (7) or a N-mono-(2-propynyl) (8) moiety were synthesized (FIG. 2) and compared to PEH with regard to their ability to inhibit GABA-T and MAO-A and -B in vitro.

It will be appreciated that compounds of the present invention can form pharmaceutically acceptable salts, such as acid addition salts. Examples of suitable acids for salt addition include hydrochloric, sulfuric, phosphoric, acetic, citric, oxalic, malonic, salicylic, malic, fumaric, succinic, ascorbic, maleic, methanesulfonic and other mineral carboxylic acids well known in the art.

Method of preparing pharmaceutically acceptable salts are well known to the skilled worker.

Methods of preparation of acid salts are know to the skilled worker. For example, the salts may be prepared by contacting the free base form with a sufficient amount of the desired acid to produce a salt in the conventional manner. The free base forms may be regenerated by treating the salt with a suitable dilute aqueous sodium hydroxide, potassium carbonate, ammonia or sodium bicarbonate. The free base forms may differ from their respective salts form somewhat in certain physical properties, such as solubility in polar solvents, but the acid and base forms are otherwise equivalent to their respective free base forms for the purpose of the present invention.

The present invention also provides pharmaceutical compositions, which comprise a therapeutically effective amount of the compound(s) of the present invention, or a pharmaceutically acceptable salt thereof and a pharmaceutically acceptable carrier. The therapeutically effective amount of the compound(s) or a pharmaceutically acceptable salt thereof is determined according to methods well known to those skilled in the art.

The compositions of the present invention may be prepared as medicaments to be administered orally, parenterally, rectally or transdermally.

The group of substituents was selected to determine positional, steric, electronic and lipophilic aryl substituent effects on neurochemical action(s) of the drugs of interest.

Since PEH appears to possess a number of potentially beneficial neurochemical properties, the drugs synthesized herein were tested to determine if they were effective prodrugs. Two of the analogs, 7p and 8p were compared to PEH with regard to their ex vivo effects on GABA-T, MAO, and levels of amino acids to determine their possible value as PEH prodrugs.

2. Results.

Figure 1:
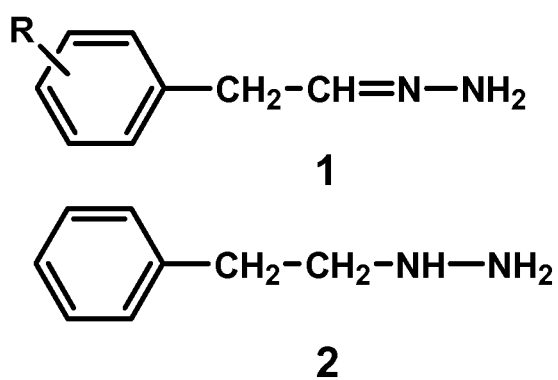
FIG. 1 depicts the structures of β-phenylethylidenehydrazine (PEH.
Figure 2:
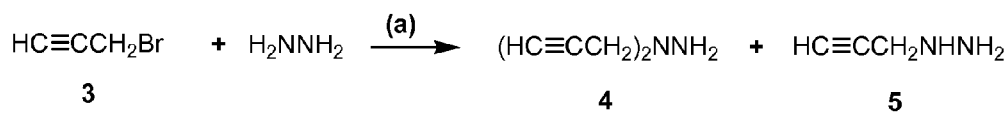
FIG. 2 depicts the synthesis of β-phenylethylidenehydrazine derivatives.
Figure 2:
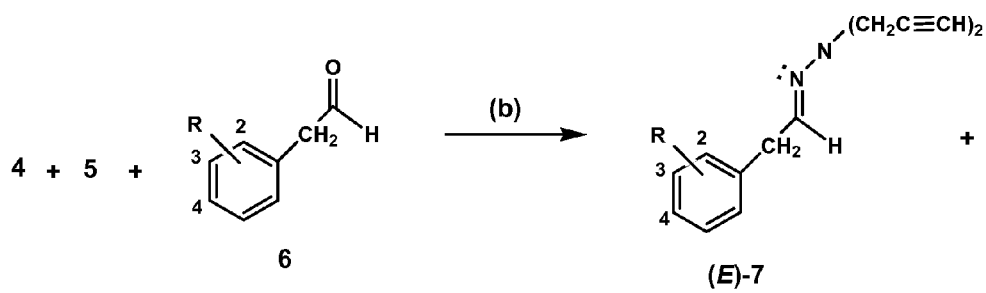
Figure 2:
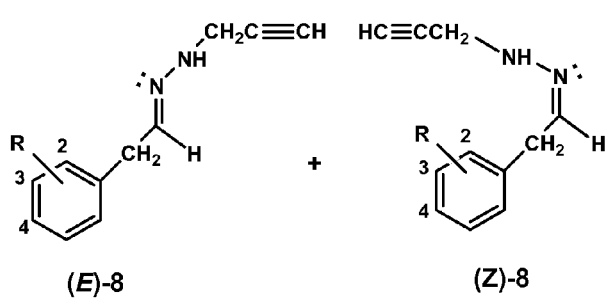

A group of β-phenylethylidenehydrazines possessing a variety of substituents (Me, OMe, Cl, F, $CF_3$) at the ortho-, meta- and para-positions of the phenyl ring, in conjunction with either a N-bis-(2-propynyl) (7) or a N-mono-(2-propynyl) (8), moiety were synthesized by condensation of the respective phenylacetaldehydes (6a-p) with a mixture of 1,1-bis-(2-propynyl)hydrazine (4) and 1-(2-propynyl)hydrazine (5) in methanol at 25° C., as illustrated in FIG. 2. The N-bis-(2-propynyl) compounds 7 were obtained as the (E)-stereoisomer in 12-18% yield. In contrast, the N-mono-(2-propynyl) compounds 8 were isolated in 18-34% yield as a mixture of the (E)-8 and (Z)-8 stereoisomers, which differ in stereochemistry about the C=N moiety; the ratio of (E):(Z) isomers was in a range between 1.6:1 to 6:1. The (E)-7, and an inseparable mixture of the (E)-8 and (Z)-8, compounds were separated by silica gel flash chromatography. The homogeneity of the N-bis-(2-propynyl) compounds 7 is supported by the fact that a single spot was observed in each case upon thin layer chromatography (TLC) using a Macherey-Nagel silica gel Polygram SIL G/$UV_{254}$ plate (0.20 mm thickness) with a development solvent that provided reproducible, similar $R_f$ values for the compounds of interest. The mixture of the (E)-8 and (Z)-8 isomers showed an inseparable spot under similar TLC conditions. The $^1H$ NMR spectra for the mixture of (E)-8 and (Z)-8 compounds exhibited dual resonances for the methylene ($CH_2$) and methine (=CH) groups. In this regard, the =CH and $CH_2$ resonances were deshielded in the (E)-isomer relative to the (7)-isomer. These shielding effects are consistent with those reported for acetaldehyde hydrazones.[37] The single spot on TLC and the combination of both proton and carbon NMR spectra, accounting for all the hydrogen and carbon atoms in the molecule, provided reliable confirmation of homogeneity and structure. In addition, 7p and 8p, which were studied ex vivo as well as in vitro for neurochemical/ pharmacological activity, were investigated on HPLC with electrochemical detection. Studies with various mobile phases on an Atlantis dC18 column (3.0×100 mm) revealed a single peak in all cases.

2.2. GABA-T

Figure 3:
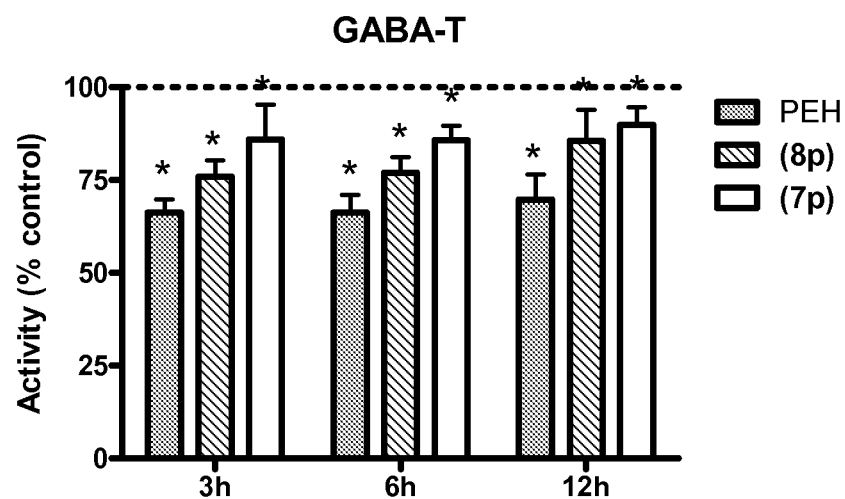
FIG. 3 is a bar graph depicting the effect of PEH, 8p and 7p on GABA-T activity.

In vitro, PEH inhibited GABA-T by approximately 50% at a concentration of 10 μM, while none of the analogs inhibited GABA-T at concentrations of either 10 μM or 100 μM (data not shown). Ex vivo, PEH significantly reduced GABA-T activity at all time points tested; activity was reduced to 66% of controls at 3 and 6 hours post-injection, and activity remained inhibited 12 hours after PEH injection (70% of control). The degree of GABA-T inhibition by PEH at this dose is consistent with previous data.[5] 7p and 8p also decreased GABA-T activity at 3 and 6 hours following drug administration, although the inhibitory effect was significantly weaker than that observed following PEH administration (86% of control for 7p at 3 and 6 hours after injection, and 76% and 77% of control for 8p at 3 and 6 hours respectively). GABA-T activity was not significantly different from control values 12 hours after 7p or 8p injection. These results are shown in FIG. 3.

2.3. MAO.

Figure 4:
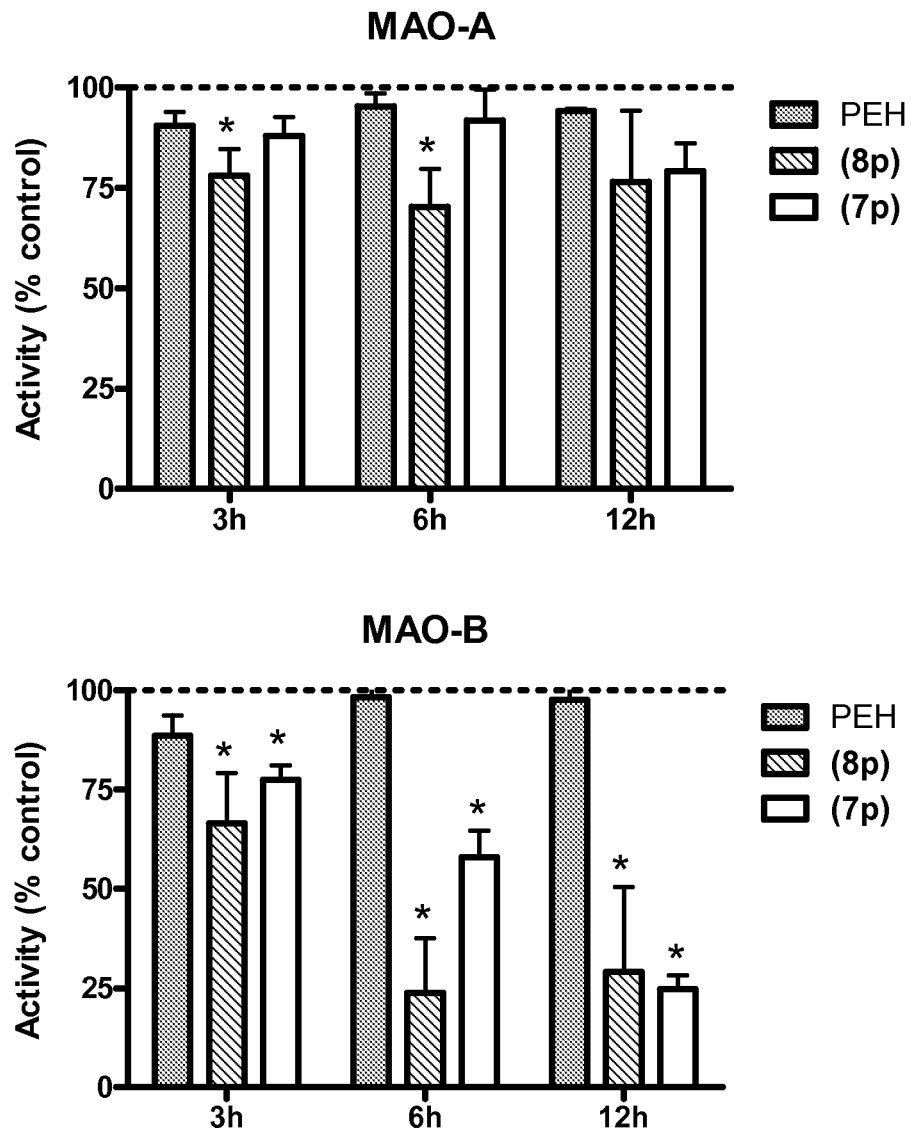
FIG. 4 is a bar graph depicting the effect of PEH, 8p and 7p on MAO-A and MAO-B activity.

In vitro, PLZ inhibited both MAO-A and -B by greater than 95%, while PEH had a much weaker effect on both MAO isoenzymes (26.7±3.1% and 14.9±6.6% inhibition (mean±SEM, n=4) for MAO-A and -B respectively). Under the same conditions, none of the analogues tested inhibited MAO-A or MAO-B by more than 15%. PEH has been shown previously to have a weak, transient effect on MAO-A and -B activity ex vivo,[5] and PEH did not alter the activity of either MAO-A or -B in brain tissue taken from PEH-treated rats. At the same dose 7p did not significantly alter MAO-A activity at any time point tested, and 8p had a weak, transient effect on MAO-A, significantly reducing activity at 3 and 6 hours following drug administration to 78% and 70% of control values (i.e. 22% and 30% inhibition), respectively. In contrast, both 7p and 8p had relatively marked inhibitory effects on MAO-B activity, significantly reducing MAO-B activity at all time points tested. These effects were particularly pronounced at 6 and 12 hours following drug injection, where MAO-B activity was reduced by 7p to 58% and 25% of control at 6 and 12 hours (respectively) and by 8p to 24% and 29% of control at 6 and 12 hours (respectively). These results are shown in FIG. 4.

2.4. Amino Acids.

Figure 5:
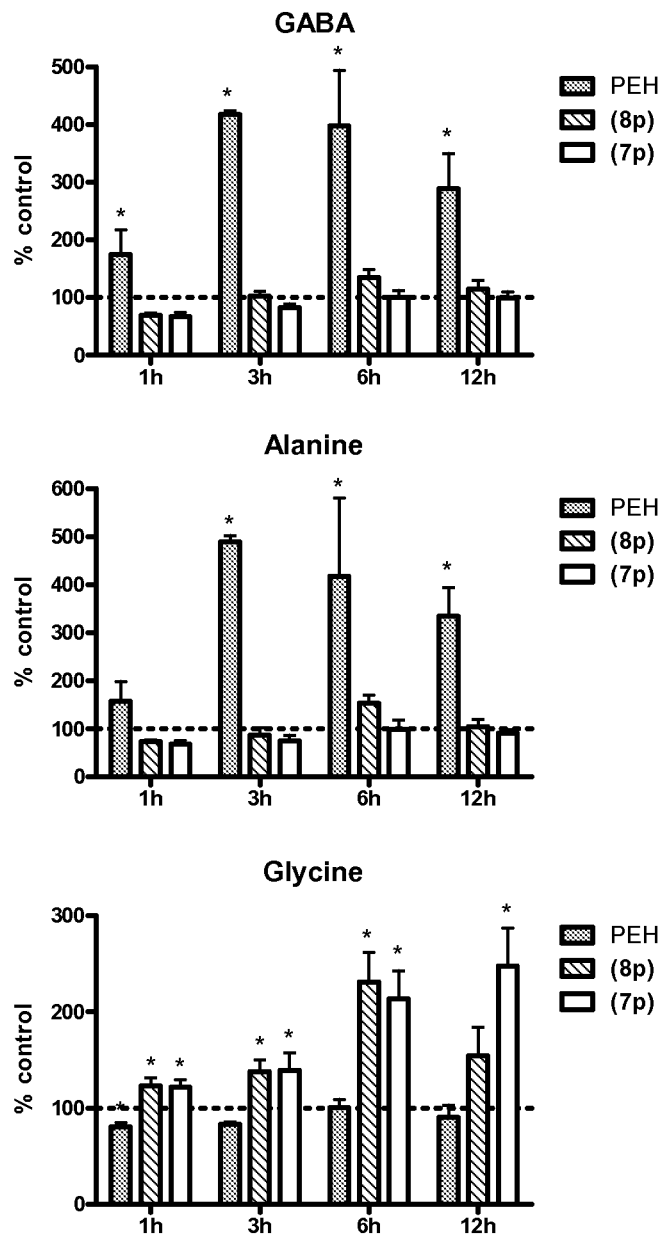
FIG. 5 is a bar graph depicting the effect of PEH, 8p and 7p on GABA, alanine and glycine levels in rat whole brain.

The ex vivo studies demonstrated that PEH increased brain GABA and alanine levels, an effect which was significant at all three timepoints following drug administration. Elevations in brain GABA and alanine were greatest at 3 hours following PEH injection, reaching 418% and 489% of control values, respectively. PEH did not significantly alter brain glutamate or glycine levels relative to controls. 8p and 7p administration did not significantly alter the levels of GABA, alanine or glutamate at any time point tested. However, 8p and 7p caused marked increases in brain glycine levels; 8p significantly increased glycine at 3 and 6 hours post-injection, reaching 216% of control at 6 hours, and 7p increased glycine at 3, 6 and 12 hours post-injection, reaching 248% of control at 12 hours. These results are shown in FIG. 5.

3. Discussion.

PEH is a putative metabolite of PLZ and is thought to contribute to some of PLZ's neurochemical and therapeutic properties. On its own, PEH has been shown to be a potent inhibitor of GABA-T, significantly elevating brain GABA levels, while its effects on MAO activity are weak and transient.[5]

As described herein, a number of PEH analogs substituted in the phenyl ring and by one or two propynyl groups at the terminal nitrogen were synthesized and tested for their effects on GABA-T and MAO in vitro. Two of the analogs (7p and 8p) were also tested ex vivo for their effects on GABA-T, MAO-A and -B and amino acids.

The neurochemical properties of PEH and those of the analogs were dissimilar. Like PLZ, PEH is an inhibitor of GABA-T (the enzyme responsible for the breakdown of GABA) and causes marked, long-lasting increases in brain levels of GABA.[5] This elevation in GABA by PLZ has been found to occur at a relatively low inhibition of GABA-T.[8,10] While 7p and 8p also inhibited GABA-T, the inhibition at the equivalent dose tested was to a significantly lesser degree than the inhibition observed following administration of PEH itself, and was apparently insufficient to significantly elevate brain GABA levels. However, while not wishing to be bound by theory, that these two analogs caused some inhibition of GABA-T activity ex vivo while being inactive in vitro suggests that some metabolic conversion of them to PEH may occur ex vivo.

PEH also elevated brain levels of alanine, while administration of 7p and 8p did not alter alanine levels. Given that the breakdown of alanine is achieved by the action of alanine transaminase (ALA-T), an enzyme structurally and functionally related to GABA-T, it has been suggested that PEH inhibits ALA-T in a similar manner to the inhibition of GABA-T, causing increased alanine levels. None of the drugs had any effect on brain levels of glutamate. However, whereas PEH did not significantly alter glycine levels, both 7p and 8p caused marked increases in brain glycine levels.

In the present experiments ex vivo, 7p and 8p had modest inhibitory effects on MAO-A at some (but not all) timepoints. However, unlike PEH, both 7p and 8p had relatively strong inhibitory effects on MAO-B, particularly 6 and 12 hours after drug administration. However, neither 7p nor 8p caused any inhibition of MAO-A or -B in vitro at a concentration of 10 μM.

As shown herein, 7p and 8p are inhibitors of MAO-B ex vivo. Other MAO-B inhibitors such as 1-deprenyl and rasagiline have been reported to be useful in treatment of neurodegenerative disorders such as Parkinson's disease (PD) and Alzheimer's disease (AD). Inhibition of MAO-B could increase brain levels of dopamine in patients suffering from PD, and could counteract the increased MAO activity and the increased MAO mRNA expression observed in AD.[38] The neuroprotective abilities of the drugs mentioned above (1-deprenyl, rasagiline) are not completely understood.

7p and 8p markedly increased brain levels of glycine. Glycine acts as an inhibitory amino acid in the brain stem and spinal cord,[40] but is also a co-agonist at the glutamate NMDA receptor,[41] and thus exerts excitatory effects in other brain areas such as the cortex and hippocampus. NMDA receptor hypofunction is believed by many to contribute to the symptoms of schizophrenia.[42] Preclinical and clinical studies have consistently demonstrated that NMDA antagonists produce a range of symptoms characteristic of the illness.[42,43] While direct glycine agonists have been reported to be useful in treating negative and possibly cognitive symptoms of schizophrenia, they have been of limited clinical utility because of the high doses required and their relatively poor penetration of the blood-brain barrier.[43] However, indirect increases in brain glycine via inhibition of glycine transporters (proteins that remove glycine from the synapse) have shown substantial promise.[43] 7p and 8p may also be used as therapeutic agents in schizophrenia, since they offer another indirect mechanism by which brain glycine is elevated (and therefore NMDA receptor activity possibly facilitated). The primary route of glycine metabolism in animals involves the glycine cleavage system (GCS), a mitochondrial complex of four enzymes that is present in many vertebrate organs, including the brain.

4. Conclusions

A number of N-mono-(propynyl) and N-bis-(2-propynyl) analogs of PEH with varying substituents in the phenyl ring were synthesized, characterized by TLC followed by proton and carbon NMR and tested for their ability to inhibit GABA-T, MAO-A and MAO-B in vitro in rat brain tissue. Two of the compounds, 7p and 8p (N-bis-(2-propynyl)PEH and N-mono (2-propynyl)PEH) were studied further by investigating their effects on brain levels of amino acids and on activities of GABA-T, MAO-A and MAO-B after intraperitoneal injection to evaluate their value as prodrugs of PEH, given that the N-propynyl group(s) in similar molecules has been shown to be removed metabolically in vivo. None of the analogs was particularly effective at inhibiting GABA-T, MAO-A or MAO-B in vitro. In the ex vivo study in rats, neither 7p or 8p produced as strong effects on inhibition of GABA-T and on elevation of brain GABA as PEH, at the dose studied. Ex vivo, 7p did not inhibit MAO-A while 8p had a weak transient effect, but both drugs inhibited MAO-B at all time intervals studied.

7p and 8p increased the brain levels of glycine (PEH produced no such increase). Glycine is a co-agonist at the excitatory NMDA glutamate receptor. The glutamatergic system has been proposed to be hypofunctional in schizophrenia, and administration of high doses of glycine to individuals with schizophrenia has been reported to improve the negative symptoms of this disorder.[43]

5. Experimental 5.1. Materials

The following chemicals were obtained from Sigma Chemical Company (St. Louis, Mo., USA): GABA, glutamate, alanine, glycine, α-ketoglutaric acid, 2-aminoethylisothiouronium, tri-n-octylamine, o-phthalaldehyde, pyridoxal phosphate, and GABAase. N-isobutyryl-L-cysteine was purchased from Novabiochem (La Jolla, Calif., USA), and $^{14}$C-β-phenylethylamine, $^{14}$C-5-hydroxytryptamine and $^{3}$H-GABA were purchased from Perkin Elmer (Waltham, Mass., USA). All other reagents were purchased from Aldrich Chemicals (Milwaukee, Wis., USA) or Fischer Scientific (Ottawa, ON, Canada).

5.2. Spectroscopy

Infrared (IR) spectra were recorded using a Nicolet 550 Series II Magna FT-IR spectrometer. Nuclear magnetic resonance ($^{1}$H NMR, $^{13}$C NMR) spectra were recorded on a Bruker AM-300 spectrophotometer. The assignment of exchangeable protons (NH) was confirmed by the addition of $D_2O$. $^{13}$C NMR spectra were acquired using the J modulated spin-echo technique where methyl and methine carbon resonances appear as positive peaks and methylene and quaternary carbon resonances appear as negative peaks. Silica gel column chromatography was performed using silica gel (70-230 mesh) purchased from Silicycle (Quebec, Canada). 1,1-bis-(2-Propynyl)hydrazine (4) and 1-(2-propynyl)hydrazine (5) were prepared by reaction of propargyl bromide (3) with hydrazine hydrate according to a patent procedure.[44] The phenylacetaldehydes 6a-n were prepared by oxidation of the corresponding phenylethyl alcohols using dipyridine chromium (VI) oxide (Collin's reagent) in dry dichloromethane at 25° C. according to reported procedures.[45,46] 4-Trifluoromethylphenethyl alcohol, which was not commercially available from Aldrich, was prepared by the lithium aluminum hydride reduction of 4-trifluoromethylphenylacetic acid using reported procedures.[47,48] The ratio of the (E)-8 and (Z)-8 stereoisomers was calculated from the integrals for the dual $CH_2$ resonances in the $^1H$ NMR spectrum.[37]

5.3. General Procedure for the Syntheses of (E)-N-bis-(2-Propynyl)-2-(2-, 3- and 4-substituted-phenyl) ethyidene]hydrazines [(E)-7], and (E)- and (Z)-N-(2-Propynyl)-2-(2-, 3- and 4-substituted-phenyl) ethylidene]hydrazines [(E)-8 and (Z)-8] (FIG. 2)

The phenylacetaldehyde (6a-p, 1.9 mmol), and a mixture (ratio of 2.3:1.0) of 1,1-bis-(2-propynyl)hydrazine (4) and 1-(2-propynyl)hydrazine (5) (0.24 g) in methanol (2 mL), were stirred at 25° C. for 2 hours. Removal of the solvent in vacuo at 25° C. afforded an oil which was separated by silica gel flash column chromatography. Petroleum ether (boiling point range of 40-60° C.) was used for all chromatographic separations. Elution with petroleum ether-ethyl acetate (98:2, v/v to 96:4, v/v ratio) gave the respective bis-(2-propynyl) hydrazine product [(E)-7]. Continued elution with petroleum ether-ethyl acetate (97:3, v/v to 88:12, v/v ratio) yielded a mixture of the respective (E)- and (Z)-mono-(2-propynyl) hydrazine stereoisomers [(E)-8 and (Z)-8]. Products [(E)-7, and the mixture of (E)-8 and (Z)-8] were stored at −78° C. prior to their use in biological studies. The % chemical yield, (E):(Z) ratio of compounds 8 at 25° C. as determined from the $^1H$ NMR integrals for the $CH_2$ resonances of the two isomers, and spectral data (IR, $^1H$ NMR, $^{13}C$ NMR) for compounds (E)-7, and (E)-8 and (Z)-8, are listed below.

5.3.1. (E)-N-bis-(2-Propynyl)-2-(2-methylphenyl) ethyidene]hydrazine [(E)-7a], and (E)- and (Z)-N-(2-Propynyl)-2-(2-methylphenyl)ethylidene]hydrazines [(E)-8a and (Z)-8a]

(E)-7a: Yellow oil separated using petroleum ether-ethyl acetate as eluant (96:4, v/v); Yield: 15%; IR (liquid film): 3294 (C≡CH), 1602 (CH=N) cm$^{-1}$; $^1H$ NMR (CDCl$_3$): δ 7.14-7.24 (m, 4H, phenyl hydrogens), 7.00 (t, J=5.7 Hz, 1H, CH$_2$CH=N), 3.96 (d, J=2.4 Hz, 4H, CH$_2$C≡CH), 3.62 (d, J=5.7 Hz, 2H, CH$_2$CH=N), 2.34 (s, 3H, CH$_3$) 2.26 (t, J=2.4 Hz, 2H, CH$_2$C≡CH); $^{13}$C NMR (CDCl$_3$): δ 141.78 (CH=N), 136.81, 135.84 (phenyl C-1, C-2), 130.24, 129.26 (phenyl C-3, C-6), 126.67, 125.99 (phenyl C-4, C-5), 73.41 (C≡CH), 61.30 (C≡CH), 42.23 (CH$_2$C≡CH), 37.38 (CH$_2$CH=N), 19.60 (CH$_3$).

(E)-8a and (Z)-8a (ratio 3.5:1): Yellow oil separated using petroleum ether-ethyl acetate (88:12, v/v); Yield: 21%; IR (liquid film): 3294 (C≡CH), 1602 (CH=N) cm$^{-1}$; (E)-8a isomer: $^1H$ NMR (CDCl$_3$): δ 7.17-7.20 (m, 4H, phenyl hydrogens), 7.06 (t, J=5.7 Hz, 1H, CH$_2$CH=N), 5.20 (br s, 1H, NH), 3.90 (d, J=2.4 Hz, 2H, CH$_2$C≡CH), 3.57 (d, J=5.7 Hz, 2H, CH$_2$CH=N), 2.34 (s, 3H, CH$_3$), 2.25 (t, J=2.4 Hz, 1H, CH$_2$C≡CH); $^{13}$C NMR (CDCl$_3$): δ 142.15 (CH=N), 136.76, 135.58 (phenyl C-1, C-2), 130.30, 129.34 (phenyl C-3, C-6), 126.76, 126.06 (phenyl C-4, C-5), 72.09 (C≡CH), 61.00 (C≡CH), 39.05 (CH$_2$C≡CH), 36.81 (CH$_2$CH=N), 19.44 (CH$_3$); (Z)-8a isomer: $^1H$ NMR (CDCl$_3$): δ 7.17-7.20 (m, 4H, phenyl hydrogens), 6.70 (t, J=4.9 Hz, 1H, CH$_2$CH=N), 5.20 (br s, 1H, NH), 4.00 (d, J=2.1 Hz, 2H, CH$_2$C≡CH), 3.42 (d, J=4.9 Hz, 2H, CH$_2$CH=N), 2.36 (s, 3H, CH$_3$), 2.31 (t, J=2.1 Hz, 1H, CH$_2$C≡CH); $^{13}$C NMR (CDCl$_3$): δ 142.85 (CH=N), 136.76, 135.58 (phenyl C-1, C-2), 130.46, 129.05 (phenyl C-3, C-6), 127.08, 125.99 (phenyl C-4, C-5), 71.80 (C≡CH), 61.00 (C≡CH), 40.45 (CH$_2$C≡CH), 31.42 (CH$_2$CH=N), 19.44 (CH$_3$).

5.3.2. (E)-N-bis-(2-Propynyl)-2-(2-methoxyphenyl) ethyidene]hydrazine [(E)-7b], and (E)- and (Z)-N-(2-Propynyl)-2-(2-methoxyphenyl)ethylidene]hydrazines [(E)-8b and (Z)-8b]

(E)-7b: Yellow oil separated using petroleum ether-ethyl acetate (96:4, v/v) as eluant; Yield: 12%; IR (liquid film): 3274 (C≡CH), 1716 (CH=N) cm$^{-1}$; $^1H$ NMR (CDCl$_3$): δ 7.20-7.26 (m, 2H, phenyl H-4, H-6), 7.10 (t, J=5.4 Hz, 1H, CH$_2$CH=N), 6.86-6.93 (m, 2H, phenyl H-3, H-5), 3.95 (d, J=2.4 Hz, 4H, CH$_2$C≡CH), 3.84 (s, 3H, OCH$_3$), 3.62 (d, J=5.4 Hz, 2H, CH$_2$CH=N), 2.25 (t, J=2.4 Hz, 2H, CH$_2$C≡CH); $^{13}$C NMR (CDCl$_3$): δ 157.35 (phenyl C-2), 143.18 (CH=N), 130.14 (phenyl C-6), 127.74 (phenyl C-4), 126.24 (phenyl C-1), 120.51 (phenyl C-5), 110.37 (phenyl C-3), 73.27 (C≡CH), 61.00 (C≡CH), 55.36 (OCH$_3$), 42.29 (CH$_2$C≡CH), 33.80 (CH$_2$CH=N).

(E)-8b and (Z)-8b (ratio 1.6:1): Yellow oil separated using petroleum ether-ethyl acetate (89:11, v/v); Yield: 27%; IR (liquid film): 3271 (C≡CH), 1595 (CH=N) cm$^{-1}$; (E)-8b isomer: $^1H$ NMR (CDCl$_3$): δ 7.13-7.28 (m, 3H, phenyl H-4, H-6, CH=N), 6.85-6.95 (m, 2H, phenyl H-3, H-5), 4.91 (br s, 1H, NH), 3.88 (d, J=2.4 Hz, 2H, CH$_2$C≡CH), 3.84 (s, 3H, OCH$_3$), 3.57 (d, J=5.4 Hz, 2H, CH$_2$CH=N), 2.25 (t, J=2.4 Hz, 1H, CH$_2$C≡CH); $^{13}$C NMR (CDCl$_3$): δ 157.32 (phenyl C-2), 143.05 (CH=N), 130.24 (phenyl C-6), 127.85 (phenyl C-4), 125.94 (phenyl C-1), 120.59 (phenyl C-5), 110.37 (phenyl C-3), 72.02 (C≡CH), 61.00 (C≡CH), 55.36 (OCH$_3$), 39.14 (CH$_2$C≡CH), 33.42 (CH$_2$CH=N); (Z)-8b isomer: $^1H$ NMR (CDCl$_3$): δ 7.13-7.28 (m, 2H, phenyl H-4, H-6), 6.85-6.95 (m, 2H, phenyl H-3, H-5), 6.72 (t, J=5.1 Hz, 1H, CH$_2$CH=N), 5.30 (br s, 1H, NH), 3.98 (d, J=2.1 Hz, 2H, CH$_2$C≡CH), 3.86 (s, 3H, OCH$_3$), 3.44 (d, J=5.1 Hz, 2H, CH$_2$CH=N), 2.28 (t, J=2.1 Hz, 1H, CH$_2$C≡CH); $^{13}$C NMR (CDCl$_3$): δ 157.32 (phenyl C-2), 143.33 (CH=N), 130.20 (phenyl C-6), 128.16 (phenyl C-4), 125.94 (phenyl C-1), 120.79 (phenyl C-5), 110.44 (phenyl C-3), 71.62 (C≡CH), 61.00 (C≡CH), 55.36 (OCH$_3$), 40.45 (CH$_2$C≡CH), 28.41 (CH$_2$CH=N).

5.3.3. (E)- and (Z)-N-(2-Propynyl)-2-(2-chlorophenyl)ethylidene]hydrazines [(E)-8c and (Z)-8c, ratio 3.1:1]

Yellow oil isolated using petroleum ether-ethyl acetate (96:4, v/v) as eluant; Yield: 34%; IR (liquid film): 3278 (C≡CH), 1602 (CH=N) cm$^{-1}$; (E)-8c isomer: $^1H$ NMR (CDCl$_3$): δ 7.18-7.42 (m, 4H, phenyl hydrogens), 7.14 (t, J=5.7 Hz, 1H, CH$_2$CH=N), 5.10 (br s, 1H, NH), 3.89 (d, J=2.4 Hz, 2H, CH$_2$C≡CH), 3.70 (d, J=5.7 Hz, 2H, CH$_2$CH=N), 2.26 (t, J=2.4 Hz, 1H, CH$_2$C≡CH); $^{13}$C NMR (CDCl$_3$): δ 140.72 (CH=N), 135.44 (phenyl C-1), 134.07 (phenyl C-2), 130.78 (phenyl C-6), 129.60 (phenyl C-3), 127.90 (phenyl C-4), 126.93 (phenyl C-5), 72.18 (C≡CH), 61.10 (C≡CH), 38.98 (CH$_2$C≡CH), 36.62 (CH$_2$CH=N); (Z)-8c isomer: $^1H$ NMR (CDCl$_3$): δ 7.18-7.42 (m, 4H, phenyl hydrogens), 6.71 (t, J=5.1 Hz, 1H, CH$_2$CH=N), 5.10 (br s, 1H, NH), 4.00 (d, J=2.1 Hz, 2H, CH$_2$C≡CH), 3.56 (d, J=5.1 Hz, 2H, CH$_2$CH=N), 2.30 (t, J=2.1 Hz, 1H, CH$_2$C≡CH); $^{13}$C NMR (CDCl$_3$): δ 140.59 (CH=N), 135.44 (phenyl C-1), 134.07 (phenyl C-2), 131.21 (phenyl C-6), 129.70 (phenyl C-3), 128.40 (phenyl C-4), 126.76 (phenyl C-5), 71.86 (C≡CH), 61.10 (C≡CH), 40.50 (CH$_2$C≡CH), 31.38 (CH$_2$CH=N).

5.3.4. (E)-N-bis-(2-Propynyl)-2-(2-fluorophenyl) ethyidene]hydrazine [(E)-7d], and (E)- and (Z)-N-(2-Propynyl)-2-(2-fluorophenyl)ethylidene]hydrazines [(E)-8d and (Z)-8d]

(E)-7d: Yellow oil separated using petroleum ether-ethyl acetate (96:4, v/v) as eluant; Yield, 18%; IR (liquid film): 3300 (C≡CH), 1710 (CH=N) cm$^{-1}$; $^1$H NMR (CDCl$_3$): δ 7.05-7.29 (m, 4H, phenyl hydrogents), 7.03 (t, J=5.7 Hz, 1H, CH$_2$CH=N), 3.97 (d, J=2.4 Hz, 4H, CH$_2$C≡CH), 3.65 (d, J=5.7 Hz, 2H, CH$_2$CH=N), 2.26 (t, J=2.4 Hz, 2H, CH$_2$C≡CH); $^{13}$C NMR (CDCl$_3$): δ 162.45 (d, $^1J_{C,F}$=246.1 Hz, C-2), 140.29 (CH=N), 130.85 (d, $^3J_{C,F}$=4.37 Hz, C-6), 128.25 (d, $^3J_{C,F}$=8.75 Hz, C-4), 124.76 (d, $^2J_{C,F}$=15.39 Hz, C-1), 124.07 (d, $^4J_{C,F}$=3.3 Hz, C-5), 115.31 (d, $^2J_{C,F}$=21.96 Hz, C-3), 73.41 (C≡CH), 61.30 (C≡CH), 42.20 (CH$_2$C≡CH), 32.63 (CH$_2$CH=N).

(E)-8d and (Z)-8d (ratio 3.7:1): Yellow oil separated using petroleum ether-ethyl acetate (94:6, v/v) as eluant; Yield, 24%; IR (liquid film): 3288 (C≡CH), 1649 (CH=N) cm$^{-1}$; (E)-8d isomer: $^1$H NMR (CDCl$_3$): δ 7.01-7.28 (m, 5H, phenyl hydrogens, CH$_2$CH=N), 5.10 (br s, 1H, NH), 3.90 (d, J=2.4 Hz, 2H, CH$_2$C≡CH), 3.61 (d, J=6.0 Hz, 2H, CH$_2$CH=N), 2.26 (t, J=2.4 Hz, 1H, CH$_2$C≡CH); $^{13}$C NMR (CDCl$_3$): δ 162.45 (d, $^1J_{C,F}$=246.1 Hz, C-2), 140.81 (CH=N), 130.78 (d, $^3J_{C,F}$=4.37 Hz, C-6), 128.30 (d, $^3J_{C,F}$=8.75 Hz, C-4), 124.50 (d, $^2J_{C,F}$=15.40 Hz, C-1), 124.03 (d, $^4J_{C,F}$=3.24 Hz, C-5), 115.44 (d, $^2J_{C,F}$=21.56 Hz, C-3), 72.11 (C≡CH), 61.30 (C≡CH), 38.88 (CH$_2$C≡CH), 32.08 (CH$_2$CH=N); (Z)-8d isomer: $^1$H NMR (CDCl$_3$): δ 7.01-7.28 (m, 4H, phenyl hydrogens), 6.75 (t, J=5.1 Hz, 1H, CH$_2$CH=N), 5.10 (br s, 1H, NH), 4.00 (d, J=2.1 Hz, 2H, CH$_2$C≡CH), 3.48 (d, J=5.1 Hz, 2H, CH$_2$CH=N), 2.30 (t, J=2.1 Hz, 1H, CH$_2$C≡CH); $^{13}$C NMR (CDCl$_3$): δ 162.45 (d, $^1J_{C,F}$=246.1 Hz, C-2), 141.50 (CH=N), 130.44 (d, $^3J_{C,F}$=3.32 Hz, C-6), 128.61 (d, $^3J_{C,F}$=7.69 Hz, C-4), 124.50 (d, $^2J_{C,F}$=15.40 Hz, C-1), 124.07 (d, $^4J_{C,F}$=3.24 Hz, C-5), 115.20 (d, $^2J_{C,F}$=17.58 Hz, C-3), 71.80 (C≡CH), 61.30 (C≡CH), 40.40 (CH$_2$C≡CH), 26.55 (CH$_2$CH=N).

5.3.5. (E)-N-bis-(2-Propynyl)-2-(2-trifluoromethylphenyl)ethyidene]hydrazine [(E)-7e], and (E)- and (Z)-N-(2-Propynyl)-2-(2-trifluoromethylphenyl)ethylidene]hydrazines [(E)-8e and (Z)-8e]

(E)-7e: Yellow oil separated using petroleum ether-ethyl acetate (96:4, v/v) as eluant; Yield, 17%; IR (liquid film): 3288 (C≡CH), 1736 (CH=N) cm$^{-1}$; $^1$H NMR (CDCl$_3$): δ 7.31-7.66 (m, 4H, phenyl hydrogens), 7.00 (t, J=5.7 Hz, 1H, CH$_2$CH=N), 3.98 (d, J=2.4 Hz, 4H, CH$_2$C≡CH), 3.80 (d, J=5.7 Hz, 2H, CH$_2$CH=N), 2.26 (t, J=2.4 Hz, 2H, CH$_2$C≡CH); $^{13}$C NMR (CDCl$_3$): δ 140.46 (CH=N), 136.10 (phenyl C-1), 131.81, 131.46 (phenyl C-5, C-6), 126.57 (phenyl C-4), 126.22 (q, $^1J_{C,F}$=270.2 Hz, CF$_3$), 125.93 (d, $^3J_{C,F}$=5.50 Hz, phenyl C-3), 121.00 (q, $^2J_{C,F}$=29.66 Hz, phenyl C-2), 73.47 (C≡CH), 61.30 (C≡CH), 42.17 (CH$_2$C≡CH), 36.10 (CH$_2$CH=N).

(E)-8e and (Z)-8e (ratio 4.3:1): Yellow oil separated using petroleum ether-ethyl acetate (92:8, v/v) as eluant; Yield, 23%; IR (liquid film): 3288 (C≡CH), 1750 (CH=N) cm$^-$; (E)-8e isomer: $^1$H NMR (CDCl$_3$): δ 7.31-7.66 (m, 4H, phenyl hydrogens), 7.09 (t, J=5.4 Hz, 1H, CH$_2$CH=N), 5.10 (br s, 1H, NH), 3.90 (d, J=2.1 Hz, 2H, CH$_2$C≡CH), 3.75 (d, J=5.4 Hz, 2H, CH$_2$CH=N), 2.26 (t, J=2.1 Hz, 1H, CH$_2$C≡CH); (Z)-8e isomer: $^1$H NMR (CDCl$_3$): δ 7.31-7.66 (m, 4H, phenyl hydrogens), 6.72 (t, J=5.1 Hz, 1H, CH$_2$CH=N), 5.10 (br s, 1H, NH), 4.00 (d, J=1.8 Hz, 2H, CH$_2$C≡CH), 3.62 (d, J=5.1 Hz, 2H, CH$_2$CH=N), 2.31 (t, J=1.8 Hz, 1H, CH$_2$C≡CH).

5.3.6. (E)-N-bis-(2-Propynyl)-2-(3-methylphenyl) ethyidene]hydrazine [(E)-7f], and (E)- and (Z)-N-(2-Propynyl)-2-(3-methylphenyl)ethylidene]hydrazines [(E)-8f and (Z)-8f]

(E)-7f: Yellow oil separated using petroleum ether-ethyl acetate as eluant (98:2, v/v); Yield, 14%; IR (liquid film): 3301 (C≡CH), 1743 (CH=N) cm$^{-1}$; $^1$H NMR (CDCl$_3$): δ 7.21 (t, J=7.3 Hz, 1H, phenyl H-5), 7.02-7.08 (m, 4H, phenyl H-2, H-4, H-6, CH$_2$CH=N), 3.98 (d, J=2.4 Hz, 4H, CH$_2$C≡CH), 3.58 (d, J=5.4 Hz, 2H, CH$_2$CH=N), 2.33 (s, 3H, CH$_3$), 2.26 (t, J=2.4 Hz, 2H, CH$_2$C≡CH); $^{13}$C NMR (CDCl$_3$): δ 142.44 (CH=N), 138.13, 137.55 (phenyl C-1, C-3), 129.64, 128.40 (phenyl C-2, C-5), 127.21 (phenyl C-4), 125.89 (phenyl C-6), 73.41 (C≡CH), 61.30 (C≡CH), 42.26 (CH$_2$C≡CH), 39.40 (CH$_2$CH=N).

(E)-8f and (Z)-8f (ratio 2.9:1): Yellow oil separated using petroleum ether-ethyl acetate (95:5, v/v) as eluant; Yield, 26%; IR (liquid film): 3301 (C≡CH), 1595 (CH=N) cm$^{-1}$; (E)-8f isomer: $^1$H NMR (CDCl$_3$): δ 7.21 (t, J=6.0 Hz, 1H, CH$_2$CH=N), 7.05-7.13 (m, 4H, phenyl hydrogens), 5.08 (br s, 1H, NH), 3.91 (d, J=2.7 Hz, 2H, CH$_2$C≡CH), 3.54 (d, J=6.0 Hz, 2H, CH$_2$CH=N), 2.34 (s, 3H, CH$_3$), 2.28 (t, J=2.7 Hz, 1H, CH$_2$C≡CH); $^{13}$C NMR (CDCl$_3$): δ 142.85 (CH=N), 138.22, 137.24 (phenyl C-1, C-3), 129.61, 128.46 (phenyl C-2, C-5), 127.86 (phenyl C-4), 125.86 (phenyl C-6), 72.13 (C≡CH), 60.30 (C≡CH), 39.10 (CH$_2$C≡CH), 38.91 (CH$_2$CH=N), 21.36 (CH$_3$); (Z)-8f isomer: $^1$H NMR (CDCl$_3$): δ 7.05-7.13 (m, 4H, phenyl hydrogens), 6.81 (t, J=5.4 Hz, 1H, CH$_2$CH=N), 5.08 (br s, 1H, NH), 3.99 (d, J=2.4 Hz, 2H, CH$_2$C≡CH), 3.43 (d, J=5.4 Hz, 2H, CH$_2$CH=N), 2.36 (s, 3H, CH$_3$), 2.30 (t, J=2.4 Hz, 1H, CH$_2$C≡CH); $^{13}$C NMR (CDCl$_3$): δ 142.85 (CH=N), 138.22, 137.24 (phenyl C-1, C-3), 129.32, 128.73 (phenyl C-2, C-5), 127.28 (phenyl C-4), 125.59 (phenyl C-6), 72.13 (C≡CH), 60.30 (C≡CH), 40.45 (CH$_2$C≡CH), 33.22 (CH$_2$CH=N), 21.36 (CH$_3$).

5.3.7. (E)-N-bis-(2-Propynyl)-2-(3-methoxyphenyl) ethyidene]hydrazine [(E)-7g], and (E)- and (Z)-N-(2-Propynyl)-2-(3-methoxyphenyl)ethylidene]hydrazines [(E)-8g and (Z)-8g]

(E)-7g: Yellow oil separated using petroleum ether-ethyl acetate as eluant (95:5, v/v); Yield, 12%; IR (liquid film): 3301 (C≡CH), 1709 (CH=N) cm$^{-1}$; $^1$H NMR (CDCl$_3$): δ 7.22 (t, J=7.3 Hz, 1H, phenyl H-5), 7.04 (t, J=5.7 Hz, 1H, CH$_2$CH=N), 6.76-6.84 (m, 3H, phenyl H-2, H-4, H-6), 3.97 (d, J=2.4 Hz, 4H, CH$_2$C≡CH), 3.80 (s, 3H, OCH$_3$), 3.59 (d, J=5.7 Hz, 2H, CH$_2$CH=N), 2.26 (t, J=2.4 Hz, 2H, CH$_2$C≡CH); $^{13}$C NMR (CDCl$_3$): δ 157.21 (phenyl C-3), 141.99 (CH=N), 139.22 (phenyl C-1), 129.45 (phenyl C-5), 121.21 (phenyl C-6), 114.49 (phenyl C-2), 112.04 (phenyl C-5), 73.47 (C≡CH), 61.30 (C≡CH), 55.21 (OCH$_3$), 42.23 (CH$_2$C≡CH), 39.56 (CH$_2$CH=N).

(E)-8g and (Z)-8g (ratio 3:1): Yellow oil separated using petroleum ether-ethyl acetate (93:7 v/v) as eluant; Yield, 18%; IR (liquid film): 3301 (C≡CH), 1595 (CH=N) cm$^{-1}$; (E)-8g isomer: $^1$H NMR (CDCl$_3$): δ 7.25 (t, J=7.3 Hz, 1H, phenyl H-5), 7.16 (t, J=6.0 Hz, 1H, CH$_2$CH=N), 6.77-6.84 (m, 3H, phenyl H-2, H-4, H-6), 5.08 (br s, 1H, NH), 3.90 (d, J=2.7 Hz, 2H, CH$_2$C≡CH), 3.80 (s, 3H$_2$OCH$_3$), 3.55 (d, J=6.0 Hz, 2H, CH$_2$CH=N), 2.27 (t, J=2.7 Hz, 1H, CH$_2$C≡CH); $^{13}$C NMR (CDCl$_3$): δ 159.78 (phenyl C-3), 142.44 (CH=N), 138.92 (phenyl C-1), 129.51 (phenyl C-5), 121.15 (phenyl C-6), 114.46 (phenyl C-2), 112.08 (phenyl C-4), 72.15 (C≡CH), 61.30 (C≡CH), 55.17 (OCH$_3$) 39.02 (CH$_2$C≡CH), 39.00 (CH$_2$CH=N); (Z)-8g isomer: $^1$H NMR (CDCl$_3$): δ 7.25 (t, J=7.3 Hz, 1H, phenyl H-5), 6.70-6.84 (m, 4H, phenyl H-2, H-4, H-6, CH=N), 5.08 (br s, 1H, NH), 3.99 (d, J=2.4 Hz, 2H, CH$_2$C≡CH), 3.81 (s, 3H, OCH$_3$), 3.44 (d, J=4.8 Hz, 2H, CH$_2$CH=N), 2.30 (t, J=2.4 Hz, 1H, CH$_2$C≡CH); $^{13}$C NMR (CDCl$_3$): δ 159.78 (phenyl C-3), 142.99 (CH=N), 138.92 (phenyl C-1), 129.69 (phenyl C-5), 120.88 (phenyl C-6), 114.27 (phenyl C-2), 112.23 (phenyl C-4), 71.81 (C≡CH), 61.30 (C≡CH), 55.17 (OCH$_3$) 40.42 (CH$_2$C≡CH), 33.32 (CH$_2$CH=N).

5.3.8. (E)-N-bis-(2-Propynyl)-2-(3-chlorophenyl) ethyidene]hydrazine [(E)-7h], and (E)- and (Z)-N-(2-Propynyl)-2-(3-chlorophenyl)ethylidene]hydrazines [(E)-8h and (Z)-8h]

(E)-7h: Yellow oil separated using petroleum ether-ethyl acetate as eluant (97:3, v/v); Yield, 12%; IR (liquid film): 3301 (C≡CH), 1650 (CH=N) cm$^{-1}$; $^1$H NMR (CDCl$_3$): δ 7.08-7.32 (m, 4H, phenyl hydrogens), 7.00 (t, J=5.7 Hz, 1H, CH$_2$CH=N), 3.99 (d, J=2.4 Hz, 4H, CH$_2$C≡CH), 3.59 (d, J=5.7 Hz, 2H, CH$_2$CH=N), 2.28 (t, J=2.4 Hz, 2H, CH$_2$C≡CH); $^{13}$C NMR (CDCl$_3$): δ 141.23 (CH=N), 139.44 (phenyl C-1), 134.35 (phenyl C-3), 129.73 (phenyl C-5), 128.93 (phenyl C-2), 126.93, 126.73 (phenyl C-4, C-6), 72.30 (C≡CH), 61.00 (C≡CH), 42.26 (CH$_2$C≡CH), 38.54 (CH$_2$CH=N).

(E)-8h and (Z)-8h (ratio 4.3:1): Yellow oil separated using petroleum ether-ethyl acetate (93:7 v/v) as eluant; Yield, 18%; IR (liquid film): 3288 (C≡CH), 1689 (CH=N) cm$^{-1}$; (E)-8h isomer: $^1$H NMR (CDCl$_3$): δ 7.10-7.31 (m, 5H, phenyl hydrogens, CH$_2$CH=N), 5.10 (br s, 1H, NH), 3.95 (d, J=2.1 Hz, 2H, CH$_2$C≡CH), 3.58 (d, J=6.0 Hz, 2H, CH$_2$CH=N), 2.33 (t, J=2.1 Hz, 1H, CH$_2$C≡CH); $^{13}$C NMR (CDCl$_3$): δ 141.23 (CH=N), 139.44 (phenyl C-1), 134.35 (phenyl C-3), 129.73 (phenyl C-5), 128.93 (phenyl C-2), 126.99, 126.72 (phenyl C-4, C-6), 72.29 (C≡CH), 61.00 (C≡CH), 38.92 (CH$_2$C≡CH), 38.54 (CH$_2$CH=N); (Z)-8h isomer: $^1$H NMR (CDCl$_3$): δ 7.10-7.31 (m, 4H, phenyl hydrogens), 6.80 (t, J=5.1 Hz, 1H, CH$_2$CH=N), 5.10 (br s, 1H, NH), 4.03 (d, J=1.8 Hz, 2H, CH$_2$C≡CH), 3.48 (d, J=5.1 Hz, 2H, CH$_2$CH=N), 2.35 (t, J=1.8 Hz, 1H, CH$_2$C≡CH); $^{13}$C NMR (CDCl$_3$): δ 141.23 (CH=N), 139.44 (phenyl C-1), 134.35 (phenyl C-3), 130.04 (phenyl C-5), 128.70 (phenyl C-2), 126.99, 126.72 (phenyl C-4, C-6), 71.87 (C≡CH), 61.00 (C≡CH), 40.44 (CH$_2$C≡CH), 32.81 (CH$_2$CH=N).

5.3.9. (E)- and (Z)-N-(2-Propynyl)-2-(3-fluorophenyl)ethylidene]hydrazines [(E)-8i and (Z)-8i, ratio 5.2:1]

Yellow oil separated using petroleum ether-ethyl acetate (93:7, v/v) as eluant; Yield, 22%; IR (liquid film): 3294 (C≡CH), 1703 (CH=N) cm$^{-1}$; (E)-8i isomer: $^1$H NMR (CDCl$_3$): δ 7.21-7.31 (m, 1H, phenyl H-5), 7.09 (t, J=6.0 Hz, 1H, CH$_2$CH=N), 6.90-7.14 (m, 3H, phenyl H-2, H-4, H-6), 5.10 (br s, 1H, NH), 3.91 (d, J=2.4 Hz, 2H, CH$_2$C≡CH), 3.56 (d, J=6.0 Hz, 2H, CH$_2$CH=N), 2.28 (t, J=2.4 Hz, 1H, CH$_2$C≡CH); $^{13}$C NMR (CDCl$_3$): δ 164.54 (d, $^1J_{C,F}$=246.1 Hz, phenyl C-3), 141.38 (CH=N), 140.01 (phenyl C-1), 129.94 (d, $^3J_{C,F}$=8.75 Hz, phenyl C-5), 124.43 (d, $^4J_{C,F}$=2.19 Hz, phenyl C-6), 115.73 (d, $^2J_{C,F}$=22.0 Hz, phenyl C-2), 113.45 (d, $^2J_{C,F}$=20.90 Hz, phenyl C-4), 72.25 (C≡CH), 60.10 (C≡CH), 38.95 (CH$_2$C≡CH), 38.62 (CH$_2$CH=N); (Z)-8i isomer: $^1$H NMR (CDCl$_3$): δ 7.21-7.31 (m, 1H, phenyl H-5), 6.90-7.14 (m, 3H, phenyl H-2, H-4, H-6), 6.78 (t, J=4.8 Hz, 1H, CH$_2$CH=N), 5.10 (br s, 1H, NH), 3.98 (d, J=2.1 Hz, 2H, CH$_2$C≡CH), 3.46 (d, J=4.8 Hz, 2H, CH$_2$CH=N), 2.30 (t, J=2.1 Hz, 1H, CH$_2$C≡CH); $^{13}$C NMR (CDCl$_3$): δ 164.54 (d, $^1J_{C,F}$=246.1 Hz, phenyl C-3), 141.95 (CH=N), 140.01 (phenyl C-1), 130.30 (d, $^3J_{C,F}$=8.75 Hz, phenyl C-5), 124.22 (d, $^4J_{C,F}$=3.30 Hz, phenyl C-6), 115.75 (d, $^2J_{C,F}$=21.96 Hz, phenyl C-2), 113.78 (d, $^2J_{C,F}$=20.90 Hz, phenyl C-4), 71.91 (C≡CH), 60.10 (C≡CH), 40.45 (CH$_2$C≡CH), 32.94 (CH$_2$CH=N).

5.3.10. (E)-N-bis-(2-Propynyl)-2-(3-trifluoromethylphenyl)ethyidene]hydrazine [(E)-7j], and (E)- and (Z)-N-(2-Propynyl)-2-(3-trifluoromethylphenyl)ethylidene]hydrazines [(E)-8j and (Z)-8j]

(E)-7j: Yellow oil separated using petroleum ether-ethyl acetate as eluant (96:4, v/v); Yield, 14%; IR (liquid film): 3294 (C≡CH), 1736 (CH=N) cm$^{-1}$; $^1$H NMR (CDCl$_3$): δ 7.32-7.54 (m, 4H, phenyl hydrogens), 7.02 (t, J=5.7 Hz, 1H, CH$_2$CH=N), 3.99 (d, J=2.4 Hz, 4H, CH$_2$C≡CH), 3.68 (d, J=5.7 Hz, 4H, CH$_2$CH=N), 2.27 (t, J=2.4 Hz, 2H, CH$_2$C≡CH); $^{13}$C NMR (CDCl$_3$): δ 140.11 (CH=N), 138.73 (phenyl C-1), 132.60 (phenyl C-6), 130.56 (q, $^2J_{C,F}$=29.66 Hz, phenyl C-3), 128.84 (phenyl C-5), 125.57 (d, $^3J_{C,F}$=3.24 Hz, phenyl C-2), 124.09 (q, $^1J_{C,F}$=272.46 Hz, C1-'$_3$), 123.32 (d, $^3J_{C,F}$=3.32 Hz, phenyl C-4), 73.62 (C≡CH), 61.50 (C≡CH), 42.15 (CH$_2$C≡CH), 39.20 (CH$_2$CH=N).

(E)-8j and (Z)-8j (ratio 6:1): Yellow oil separated using petroleum ether-ethyl acetate (90:10, v/v) as eluant; Yield, 21%; IR (liquid film): 3301 (C≡CH), 1736 (CH=N) cm$^{-1}$; (E)-8j isomer: $^1$H NMR (CDCl$_3$): δ 7.39-7.52 (m, 4H, phenyl hydrogens), 7.21 (t, J=5.4 Hz, 1H, CH$_2$CH=N), 5.12 (br s, 1H, NH), 3.92 (d, J=2.7 Hz, 2H, CH$_2$C≡CH), 3.63 (d, J=5.4 Hz, 2H, CH$_2$CH=N), 2.28 (t, J=2.7 Hz, 1H, CH$_2$C≡CH); $^{13}$C NMR (CDCl$_3$): δ 140.11 (CH=N), 138.73 (phenyl C-1), 132.60 (phenyl C-6), 130.56 (q, $^2J_{C,F}$=29.66 Hz, phenyl C-3), 128.86 (phenyl C-5), 125.57 (d, $^3J_{C,F}$=3.24 Hz, C$_2$ aryl), 124.08 (q, $^1J_{C,F}$=272.46 Hz, CF$_3$), 123.32 (d, $^3J_{C,F}$=3.32 Hz, phenyl C-4), 73.62 (C≡CH), 61.50 (C≡CH), 42.15 (CH$_2$C≡CH), 39.20 (CH$_2$CH=N); (Z)-8j isomer: $^1$H NMR (CDCl$_3$): δ 7.39-7.52 (m, 4H, phenyl hydrogens), 6.77 (t, J=5.1 Hz, 1H, CH$_2$CH=N), 5.12 (br s, 1H, NH), 4.00 (d, J=2.4 Hz, 2H, CH$_2$C≡CH), 3.52 (d, J=5.1 Hz, 2H, CH$_2$CH=N), 2.30 (t, J=2.4 Hz, 1H, CH$_2$C≡CH); $^{13}$C NMR (CDCl$_3$): δ 140.11 (CH=N), 138.73 (phenyl C-1), 132.30 (phenyl C-6), 130.56 (q, $^2J_{C,F}$=29.66 Hz, phenyl C-3), 129.26 (phenyl C-5), 125.37 (phenyl C-2), 124.08 (q, $^1J_{C,F}$=272.46 Hz, CF$_3$), 123.54 (d, $^3J_{C,F}$=3.24 Hz, phenyl C-4), 73.62 (C≡CH), 61.50 (C≡CH), 40.45 (CH$_2$C≡CH), 33.60 (CH$_2$CH=N).

5.3.11. (E)-N-bis-(2-Propynyl)-2-(4-methylphenyl) ethyidene]hydrazine [(E)-7k], and (E)- and (Z)-N-(2-Propynyl)-2-(4-methylphenyl)ethylidene]hydrazines [(E)-8k and (Z)-8k]

(E)-7k: Yellow oil separated using petroleum ether-ethyl acetate as eluant (98:2, v/v); Yield, 18%; IR (liquid film): 3287 (C≡CH), 1517 (CH=N) cm$^{-1}$; $^1$H NMR (CDCl$_3$): δ 7.10-7.18 (m, 4H, phenyl hydrogens), 7.03 (t, J=5.7 Hz, 1H, CH$_2$CH=N), 3.97 (d, J=2.4 Hz, 4H, CH$_2$C≡CH), 3.58 (d, J=5.7 Hz, 2H, CH$_2$CH=N), 2.33 (s, 3H, CH$_3$), 2.26 (t, J=2.4 Hz, 2H, CH$_2$C≡CH); $^{13}$C NMR (CDCl$_3$): δ 142.59

(CH=N), 136.02 (phenyl C-4), 134.48 (phenyl C-1), 129.28, 129.19 (phenyl C-2, C-6, C3-, C-5), 73.43 (C≡CH), 61.26 (C≡CH), 42.21 (CH$_2$C≡CH), 39.11 (CH$_2$CH=N), 21.04 (CH$_3$).

(E)-8k and (Z)-8k (ratio 3.4:1): Yellow oil separated using petroleum ether-ethyl acetate (90:10 v/v) as eluant; Yield, 21%; IR (liquid film): 3301 (C≡CH), 1703 (CH=N) cm$^{-1}$; (E)-8k isomer: $^1$H NMR (CDCl$_3$): δ 7.09-7.26 (m, 5H, phenyl hydrogens, CH$_2$CH=N), 5.06 (br s, 1H, NH), 3.91 (d, J=2.4 Hz, 2H, CH$_2$C≡CH), 3.53 (d, J=5.7 Hz, 2H, CH$_2$CH=N), 2.33 (s, 3H, CH$_3$), 2.27 (t, J=2.4 Hz, 1H, CH$_2$C≡CH); $^{13}$C NMR (CDCl$_3$): δ 142.89 (CH=N), 136.09 (phenyl C-4), 134.27 (phenyl C-1), 129.25 (phenyl C-2, C-6), 128.73 (phenyl C-3, C-5), 72.83 (C≡CH), 61.26 (C≡CH), 39.07 (CH$_2$C≡CH), 38.92 (CH$_2$CH=N), 21.03 (CH$_3$); (Z)-8k isomer: $^1$H NMR (CDCl$_3$): δ 7.09-7.26 (m, 4H, phenyl hydrogens), 6.80 (t, J=5.4 Hz, 1H, CH$_2$CHN), 5.06 (br s, 1H, NH), 3.98 (d, J=2.1 Hz, 2H, CH$_2$C≡CH), 3.43 (d, J=5.4 Hz, 2H, CH$_2$CH=N), 2.34 (s, 3H, CH$_3$), 2.30 (t, J=2.1 Hz, 1H, CH$_2$C≡CH); $^{13}$C NMR (CDCl$_3$): δ 142.89 (CH=N), 136.09 (phenyl C-4), 134.27 (phenyl C-1), 129.51 (phenyl C-2, C-6), 128.45 (phenyl C-3, C-5), 72.12 (C≡CH), 61.26 (C≡CH), 40.45 (CH$_2$C≡CH), 32.87 (CH$_2$CH=N), 21.03 (CH$_3$).

5.3.12. (E)-N-bis-(2-Propynyl)-2-(4-methoxyphenyl) ethyidene]hydrazine [(E)-7l], and (E)- and (Z)-N-(2-Propynyl)-2-(4-methoxyphenyl)ethylidene]hydrazines [(E)-8l and (Z)-8l]

(E)-7l: Yellow oil separated using petroleum ether-ethyl acetate as eluant (94:6, v/v); Yield, 15%; IR (liquid film): 3287 (C≡CH), 1607 (CH=N) cm$^{-1}$; $^1$H NMR (CDCl$_3$): δ 7.11-7.15 (d, J=8.7 Hz, 2H, phenyl H-2, H-6), 7.03 (t, J=5.7 Hz, 1H, CH$_2$CH=N), 6.84-6.89 (d, J=8.7 Hz, 2H, phenyl H-3, H-5), 3.96 (d, J=2.4 Hz, 4H, CH$_2$C≡CH), 3.80 (s, 3H, OCH$_3$), 3.56 (d, J=5.7 Hz, 2H, CH$_2$CH=N), 2.26 (t, J=2.4 Hz, 2H, CH$_2$C≡CH); $^{13}$C NMR (CDCl$_3$): δ 158.28 (phenyl C-4) 142.70 (CH=N), 129.82 (phenyl C-2, C-6), 129.58 (phenyl C-1), 113.96 (phenyl C-3, C-5), 73.44 (C≡CH), 61.10 (C≡CH), 55.29 (OCH$_3$), 42.23 (CH$_2$C≡CH), 38.66 (CH$_2$CH=N).

(E)-8l and (Z)-8l (ratio 3.3:1): Yellow oil separated using petroleum ether-ethyl acetate (93:7, v/v) as eluant; Yield, 25%; IR (liquid film): 3287 (C≡CH), 1607 (CH=N) cm$^{-1}$; (E)-8l isomer: $^1$H NMR (CDCl$_3$): δ 7.15-7.19 (m, 2H, phenyl H-2, H-6), 7.10 (t, J=5.7 Hz, 1H, CH$_2$CH=N), 6.83-6.89 (m, 2H, phenyl H-3, H-5), 5.05 (br s, 1H, NH), 3.90 (d, J=2.4 Hz, 2H, CH$_2$C≡CH), 3.80 (s, 3H, OCH$_3$), 3.51 (d, J=5.7 Hz, 2H, CH$_2$CH=N), 2.27 (t, J=2.4 Hz, 1H, CH$_2$C≡CH); $^{13}$C NMR (CDCl$_3$): δ 158.40 (phenyl C-4), 143.10 (CH=N), 129.82 (phenyl C-2, C-6), 129.58 (phenyl C-1), 114.03 (phenyl C-3, C-5), 72.15 (C≡CH), 61.10 (C≡CH), 55.30 (OCH$_3$), 39.10 (CH$_2$C≡CH), 38.12 (CH$_2$CH=N); (Z)-8l isomer: $^1$H NMR (CDCl$_3$): δ 7.15-7.19 (m, 2H, phenyl H-2, H-6), 6.83-6.89 (m, 2H, phenyl H-3, H-5), 6.79 (t, J=5.1 Hz, 1H, CH$_2$CH=N), 5.05 (br s, 1H, NH), 3.99 (d, J=2.1 Hz, 2H, CH$_2$C≡CH), 3.81 (s, 3H, OCH$_3$), 3.41 (d, J=5.1 Hz, 2H, CH$_2$CH=N), 2.29 (t, J=2.1 Hz, 1H, CH$_2$C≡CH); $^{13}$C NMR (CDCl$_3$): δ 158.40 (phenyl C-4), 143.10 (CH=N), 129.55 (phenyl C-2, C-6), 129.58 (phenyl C-1), 114.30 (phenyl C-3, C-5), 72.15 (C≡CH), 61.10 (C≡CH), 55.30 (OCH$_3$), 40.45 (CH$_2$C≡CH), 23.38 (CH$_2$CH=N).

5.3.13. (E)-N-bis-(2-Propynyl)-2-(4-chlorophenyl) ethyidene]hydrazine [(E)-7m], and (E)- and (Z)-N-(2-Propynyl)-2-(4-chlorophenyl)ethylidene]hydrazines [(E)-8m and (Z)-8m]

(E)-7m: Yellow oil separated using petroleum ether-ethyl acetate as eluant (97:3, v/v); Yield, 16%; IR (liquid film): 3302 (C≡CH), 1727 (CH=N) cm$^{-1}$; $^1$H NMR (CDCl$_3$): δ 7.28 (d, J=8.4 Hz, 2H, phenyl H-3, H-5), 7.18 (d, J=8.4 Hz, 2H, phenyl H-2, H-6), 7.00 (t, J=5.7 Hz, 1H, CH$_2$CH=N), 3.97 (d, J=2.4 Hz, 4H, CH$_2$C≡CH), 3.58 (d, J=5.7 Hz, 2H, CH$_2$CH=N), 2.26 (t, J=2.4 Hz, 2H, CH$_2$C≡CH); $^{13}$C NMR (CDCl$_3$): δ 140.97 (CH=N), 136.15 (phenyl C-1), 132.17 (phenyl C-4), 130.87 (phenyl C-2, C-6), 128.59 (phenyl C-3, C-5), 73.52 (C≡CH), 61.30 (C≡CH), 42.18 (CH$_2$C≡CH), 38.85 (CH$_2$CH=N).

(E)-8m and (Z)-8m (ratio 4.1:1): Yellow oil separated using petroleum ether-ethyl acetate (93:7, v/v) as eluant; Yield, 32%; IR (liquid film): 3299 (C≡CH), 1698 (CH=N) cm$^{-1}$; (E)-8m isomer: $^1$H NMR (CDCl$_3$): δ 7.28 (d, J=8.4 Hz, 2H, phenyl H-3, H-5), 7.16 (d, J=8.4 Hz, 2H, phenyl H-2, H-6), 7.07 (t, J=5.4 Hz, 1H, CH$_2$CH=N), 5.10 (br s, 1H, NH), 3.89 (d, J=2.4 Hz, 2H, CH$_2$C≡CH), 3.53 (d, J=5.7 Hz, 2H, CH$_2$CH=N), 2.26 (t, J=2.4 Hz, 1H, CH$_2$C≡CH); $^{13}$C NMR (CDCl$_3$): δ 142.5 (phenyl C-1), 141.60 (CH=N), 136.00 (phenyl C-4), 130.08 (phenyl C-2, C-6), 128.59 (phenyl C-3, C-5), 72.50 (C≡CH), 60.30 (C≡CH), 38.91 (CH$_2$C≡CH), 38.22 (CH$_2$CH=N); (Z)-8m isomer: $^1$H NMR (CDCl$_3$): δ 7.28 (d, J=8.4 Hz, 2H, phenyl H-3, H-5), 7.16 (d, J=8.4 Hz, 2H, phenyl H-2, H-6), 6.75 (t, J=4.8 Hz, 1H, CH$_2$CH=N), 5.10 (br s, 1H, NH), 3.98 (d, J=2.1 Hz, 2H, CH$_2$C≡CH), 3.42 (d, J=4.8 Hz, 2H, CH$_2$CH=N), 2.29 (t, J=2.1 Hz, 1H, CH$_2$C≡CH); $^{13}$C NMR (CDCl$_3$): δ 142.5 (phenyl C-1), 141.60 (CH=N), 136.00 (phenyl C-4), 128.90 (phenyl C-2, C-6), 128.80 (phenyl C-3, C-5), 72.50 (C≡CH), 60.30 (C≡CH), 38.91 (CH$_2$C≡CH), 38.22 (CH$_2$CH=N).

5.3.14. (E)- and (Z)-N-(2-Propynyl)-2-(4-fluorophenyl)ethylidene]hydrazines [(E)-8n and (Z)-8n, ratio 3.9:1]

Yellow oil separated using petroleum ether-ethyl acetate (92:8, v/v) as eluant; Yield, 21%; IR (liquid film): 3290 (C≡CH), 1700 (CH=N) cm$^{-1}$; (E)-8n isomer: $^1$H NMR (CDCl$_3$): δ 7.14-7.24 (m, 2H, phenyl H-2, H-6), 7.16 (t, J=6.0 Hz, 1H, CH$_2$CH=N), 6.92-7.01 (m, 2H, phenyl H-3, H-5), 5.03 (br s, 1H, NH), 3.54 (d, J=6.0 Hz, 2H, CH$_2$CH=N), 2.27 (t, J=2.4 Hz, 1H, CH$_2$C≡CH); $^{13}$C NMR (CDCl$_3$): δ 163.26 (d, $^1J_{C,F}$=243.89 Hz, C$_4$ aryl), 142.18 (CH=N), 135.00 (phenyl C-1), 130.22 (d, $^3J_{C,F}$=7.69 Hz, phenyl C-2, C-6), 115.35 (d, $^2J_{C,F}$=20.88 Hz, phenyl C-3, C-5), 72.19 (C≡CH), 60.00 (C≡CH), 39.02 (CH$_2$C≡CH), 38.17 (CH$_2$CH=N); (Z)-8n isomer: $^1$H NMR (CDCl$_3$): δ 7.14-7.24 (m, 2H, phenyl H-2, H-6), 6.92-7.01 (m, 2H, phenyl H-3, H-5), 6.77 (t, J=4.8 Hz, 1H, CH$_2$CH=N), 5.03 (br s, 1H, NH), 3.99 (d, J=2.1 Hz, 2H, CH$_2$C≡CH), 3.43 (d, J=4.8 Hz, 2H, CH$_2$CH=N), 2.30 (t, J=2.1 Hz, 1H, CH$_2$C≡CH); $^{13}$C NMR (CDCl$_3$): δ 163.26 (d, $^1J_{C,F}$=243.89 Hz, phenyl C-4), 142.18 (CH=N), 135.00 (phenyl C-1), 130.20 (d, $^3J_{C,F}$=7.69 Hz, phenyl C-2, C-6), 115.23 (d, $^2J_{C,F}$=20.88 Hz, phenyl C-3, C-5), 72.19 (C≡CH), 60.00 (C≡CH), 40.50 (CH$_2$C≡CH), 31.50 (CH$_2$CH=N).

5.3.15. (E)- and (Z)-N-(2-Propynyl)-2-(4-trifluoromethylphenyl)ethylidene]hydrazines [(E)-8o and (Z)-8o, ratio 5.4:1]

Yellow oil separated using petroleum ether-ethyl acetate (90:10, v/v) as eluant; Yield, 22%; IR (liquid film): 3295 (C≡CH), 1645 (CH=N) cm$^{-1}$; (E)-8o isomer: $^1$H NMR (CDCl$_3$): δ 7.54-7.62 (m, 2H, phenyl H-3, H-5), 7.30-7.38 (m, 2H, phenyl H-2, H-6), 7.10 (t, J=5.7 Hz, 1H, CH$_2$CH=N), 5.06 (br s, 1H, NH), 3.91 (d, J=2.4 Hz, CH$_2$C≡CH), 3.63 (d, J=5.7 Hz, 2H, CH$_2$CH=N), 2.28 (t, J=2.4 Hz, 1H, CH$_2$C≡CH); (Z)-8o isomer: $^1$H NMR (CDCl$_3$): δ 7.54-7.62 (m, 2H, phenyl H-3, H-5), 7.30-7.38 (m, 2H, phenyl H-2, H-6), 6.77 (t, J=4.8 Hz, 1H, CH$_2$CH=N), 5.06 (br s, 1H, NH), 4.00 (d, J=2.1 Hz, 2H, CH$_2$C≡CH), 3.52 (d, J=4.8 Hz, 2H, CH$_2$CH=N), 2.31 (t, J=2.1 Hz, 1H, CH$_2$C≡CH.

5.3.16. (E)-N-bis-(2-Propynyl)-2-(phenyl)ethyidene] hydrazine [(E)-7p], and (E)- and (Z)-N-(2-Propynyl)-2-(phenyl)ethylidene]hydrazines [(E)-8p and (Z)-8p]

(E)-7p: Yellow oil separated using petroleum ether-ethyl acetate as eluant (96:4, v/v); Yield, 16%; IR (liquid film): 3299 (C≡CH), 1726 (CH=N) cm$^{-1}$; $^1$H NMR (CDCl$_3$): δ 7.21-7.33 (m, 5H, phenyl hydrogens), 7.05 (t, J=5.4 Hz, 1H, CH$_2$CH=N), 3.98 (d, J=2.4 Hz, 4H, CH$_2$C≡CH), 3.62 (d, J=5.4 Hz, 2H, CH$_2$CH=N), 2.27 (t, J=2.4 Hz, 2H, CH$_2$C≡CH); $^{13}$C NMR (CDCl$_3$): δ 158.89 (CH=N), 137.21 (phenyl C-1), 128.39 (phenyl C-2, C-6), 128.04 (phenyl C-3, C5), 126.00 (phenyl C-4) 73.01 (C≡CH), 61.00 (C≡CH), 41.76 (CH$_2$C≡CH), 39.07 (CH$_2$CH=N).

(E)-8p and (Z)-8p (ratio 3.4:1): Yellow oil separated using petroleum ether-ethyl acetate (92:8, v/v) as eluant; Yield, 32%; IR (liquid film): 3281 (C≡CH), 1649 (CH=N) cm$^{-1}$; (E)-8p isomer: $^1$H NMR (CDCl$_3$): δ 7.22-7.37 (m, 5H, phenyl hydrogens), 7.13 (t, J=5.7 Hz, 1H, CH$_2$CH=N), 5.08 (br s, 1H, NH), 3.90 (d, J=2.7 Hz, 2H, CH$_2$C≡CH), 3.57 (d, J=5.7 Hz, 2H, CH$_2$CH=N), 2.27 (t, J=2.7 Hz, 1H, CH$_2$C≡CH); $^{13}$C NMR (CDCl$_3$): δ 142.63 (CH=N), 137.37 (phenyl C-1), 128.84 (phenyl C-2, C-6), 128.58 (phenyl C-3, C-5), 126.54 (phenyl C-4), 72.16 (C≡CH), 60.15 (C≡CH), 39.07 (CH$_2$C≡CH), 39.00 (CH$_2$CH=N); (Z)-8p isomer: $^1$H NMR (CDCl$_3$): δ 7.22-7.37 (m, 5H, phenyl hydrogens), 6.82 (t, J=4.8 Hz, 1H, CH$_2$CH=N), 5.08 (br s, 1H, NH), 3.99 (d, J=2.4 Hz, 2H, CH$_2$C≡CH), 3.47 (d, J=4.8 Hz, 2H, CH$_2$CH=N), 2.30 (t, J=2.4 Hz, 1H, CH$_2$C≡CH); $^{13}$C NMR (CDCl$_3$): δ 143.17 (CH=N), 137.37 (phenyl C-1), 128.84 (phenyl C-2, C-6), 128.58 (phenyl C-3, C-5), 126.79 (phenyl C-4), 71.83 (C≡CH), 60.15 (C≡CH), 40.45 (CH$_2$C≡CH), 33.29 (CH$_2$CH=N).

5.4. Neurochemical Studies

Male Sprague-Dawley rats (approximately 300 g) were pair-housed in polycarbonate cages with free access to food (Purina Rat Chow) and water, and were maintained on a 12-hour light-dark cycle (lights on at 0800). All animal procedures were approved by the University of Alberta Biosciences Animal Policy and Welfare Committee, and were carried out in accordance with the guidelines of the Canadian Council on Animal Care.

In the ex vivo studies, animals were injected intraperitoneally with equimolar amounts of PEH (30 mg/kg), 7p (47 mg/kg) or 8p (38.5 mg/kg) or vehicle (corn oil) and were killed by decapitation 3, 6 or 12 hours following drug administration. Brains were rapidly removed and flash-frozen in 2-methylbutane on solid carbon dioxide, and were stored at −80° C. Subsequently, partially-thawed brains were homogenized in 5 volumes of ice-cold distilled water, and stored in aliquots at -80° C. for use in subsequent analyses (GABA-T, MAO-A, MAO-B, and brain levels of amino acids) after addition to the appropriate buffer medium.

5.4.2. GABA-T

A modification of the colorimetric method of Sethi[49] was used in the initial in vitro screen. Brain homogenate from control rats was pre-incubated with the drug of interest and an incubation buffer before conducting the assay. In the ex vivo study of homogenates from brains of rats treated with the analogs, GABA-T activity was measured using the radiochemical procedure of Sterri and Fonnum.[20] Briefly, homogenates were incubated with radiolabelled GABA in a buffer containing pyridoxal phosphate and the resultant products were isolated using a liquid anion exchanger (tri-n-octylamine). Radioactivity (dpm) was counted using a Beckman LS 7500 liquid scintillation spectrometer.

5.4.3. MAO

Monoamine oxidase activity was determined using a modified protocol described by Lyles and Callingham.[51] In the in vitro studies, the drugs were pre-incubated with control rat brain homogenate prior to conducting the assay. Briefly, tissue homogenate was diluted in KH$_2$PO$_4$ (0.2M), and an aliquot (50 μl) was incubated with the appropriate radiolabelled substrates ($^{14}$C-labelled 5-hydroxytryptamine and β-phenylethylamine were used as substrates for MAO-A and -B respectively). The reaction products were extracted by a mixture of ethyl acetate and toluene (1:1 v/v), and a portion of the top layer was added to a vial containing scintillation fluid for radioactivity measurement. Radioactivity (dpm) was counted using a Beckman LS 7500 liquid scintillation spectrometer.

5.4.4. Amino Acid Analysis Using HPLC

Amino acid levels (GABA, glutamate, alanine and glycine) were determined using a modified procedure previously described by Grant and colleagues[52] for the quantification of amino acids using HPLC combined with fluorescence detection, following derivatization with fluoraldehyde reagent [o-phthaldialdehyde (OPA)] and isobutyryl-L-cysteine (IBLC). Briefly, a portion of the homogenate (100 μl) was added to ice-cold methanol (400 μl), re-homogenized and centrifuged (13,000 g, 4° C.). The supernatants were further diluted by a factor of 2 in ice-cold water, and transferred to HPLC vials. A portion of the supernatant (5 μl) was reacted with OPA/IBLC (5 μl) in the injection loop of a Waters Alliance 2690XE system for 1.5 minutes before injection onto the analytical column (Symmetry C$_{18}$ 5 μm (4.6×150 mm)), connected to a Symmetry C$_{18}$ guard column, held at 30° C. A Waters 474 fluorescence detector was set to an excitation wavelength of 344 nm and an emission wavelength of 443 nm. Data were collected and analyzed using the Empower Pro software package (Waters).

5.4.5. Statistics

Data were analyzed by analysis of variance (ANOVA), followed by the Newman-Keuls test. Statistical significance was established using a probability value of <0.05.

REFERENCES

1. Patek, D. R.; Hellerman, L. *J Biol Chem.* 1974, 249, 2373-2380.
2. Tipton, K. F. *Biochem J.* 1972, 128, 913-919.
3. Tipton, K. F.; Spires, I. P. *Biochem Pharmacol.* 1972, 21, 268-270.
4. Yu, P. H.; Tipton, K. F. *Biochem Pharmacol.* 1989, 38, 4245-4251.
5. Paslawski, T.; Knaus, E.; Iqbal, N.; Coutts, R. T.; Baker, G. *Drug Devel Res.* 2001, 54, 35-39.

6. Parent, M. B.; Master, S.; Kashlub, S.; Baker, G. B. *Biochem Pharmacol.* 2002, 63, 57-64.
7. MacKenzie, E. M.; Baker, G. B. (unpublished),
8. Popov, N.; Matthies, H. *J Neurochem.* 1969, 16, 899-907.
9. MacKenzie, E. M.; Grant, S. L.; Baker, G. B.; Wood, P. L. *Neurochem Res.* 2008, 33, 430-436.
10. Todd, K. G.; Baker, G. B. *J Affect Disord.* 1995, 35, 125-129.
11. Paslawski, T.; Treit, D.; Baker, G. B.; George, M.; Coutts, R. T. *Psychopharmacology (Berl).* 1996, 127, 19-24.
12. Wood, P. L.; Khan, M. A.; Moskal, J. R.; Todd, K. G.; Tanay, V. A.; Baker, G. *Brain Res.* 2006, 1122, 184-190.
13. Tanay, V. A.; Todd, K. G.; Baker, G. B. *Int J Neuropsychopharmacol.* 2002, 5, S94.
14. Yang, J.; Shen, *J. Neuroscience.* 2005, 135, 927-937.
15. Michael-Titus, A. T.; Bains, S.; Jeetle, J.; Whelpton, R. *Neuroscience.* 2000, 100, 681-684.
16. Baker, G. B.; Wong, J. T.; Yeung, J. M.; Coutts, R. T. *J Affect Disord.* 1991, 21, 207-211.
17. McKenna, K. F.; Baker, G. B.; Coutts, R. T. Naunyn Schmiedeberg's *Arch Pharmacol.* 1991, 343, 478-482.
18. McManus, D. J.; Baker, G. B.; Martin, I. L.; Greenshaw, A. J.; McKenna, K. F. *Biochem Pharmacol.* 1992, 43, 2486-2489.
19. Parent, M. B.; Habib, M. K.; Baker, G. B. *Biochem Pharmacol.* 2000, 59, 1253-1263.
20. Parent, M. B.; Habib, M. K.; Baker, G. B. *Psychopharmacology (Berl).* 1999, 142, 280-288.
21. Paslawski, T. M.; Sloley, B. D.; Baker, G. B. *Prog Brain Res.* 1995, 106, 181-186.
22. Am, O. B.; Amit, T.; Youdim, M. B. *Neurosci Lett.* 2004, 355, 169-172.
23. Bach, M. V.; Coutts, R. T.; Baker, G. B. *Xenobiotica.* 2000, 30, 297-306.
24. Durden, D. A.; Philips, S. R.; Boulton, A. A. *Biochem Pharmacol.* 1975, 24, 1365-1372.
25. Heinonen, E. H.; Myllyla, V.; Sotaniemi, K.; Lamintausta, R.; Salonen, J. S.; Anttila, M.; Savijarvi, M.; Kotila, M.; Rinne, U. K. *Acta Neurol Scand Suppl.* 1989, 126, 93-99.
26. Kalasz, H.; Kerecsen, L.; Knoll, J.; Pucsok, J. *J Chromatogr.* 1990, 499, 589-599.
27. Pirisino, R.; Ciottoli, G. B.; Buffoni, F.; Anselmi, B.; Curradi, C. *Br J Clin Pharmacol.* 1978, 7, 595-598.
28. Reynolds, G. P.; Riederer, P.; Sandler, M.; Jellinger, K.; Seemann, D. *J Neural Transm.* 1978, 43, 271-277.
29. Shin, H. S. *Drug Metab Dispos.* 1997, 25, 657-662.
30. Weli, A. M.; Lindeke, B. *Biochem Pharmacol.* 1985, 34, 1993-1998.
31. Weli, A. M.; Lindeke, B. *Xenobiotica.* 1986, 16, 281-288.
32. Yoshida, T.; Yamada, Y.; Yamamoto, T.; Kuroiwa, Y. *Xenobiotica.* 1986, 16, 129-136.
33. Philips, S. R. *J Pharm Pharmacol.* 1981, 33, 739-741.
34. Rittenbach, K. A.; Holt, A.; Ling, L.; Shan, J.; Baker, G. B. *Cell Mol Neurobiol.* 2007, 27, 179-190.
35. Rao, T. S.; Baker, G. B.; Coutts, R. T. *Brain Res Bull.* 1987, 19, 47-55.
36. Rao, T. S.; Baker, G. B.; Coutts, R. T. *Naunyn Schmiedebergs Arch Pharmacol.* 1987, 336, 25-32.
37. Karabats, G. J.; Osborne, C. E. *Tetrahedron.* 1968, 24, 3361-&.
38. Emilsson, L.; Saetre, P.; Balciuniene, J.; Castensson, A.; Cairns, N.; Jazin, E. E. *Neurosci Lett.* 2002, 326, 56-60.
39. Ling, L.; Urichuk, L.; Sloley, B. D.; Coutts, R. T.; Baker, G.; Shan, J. J.; Pang, P. K. T. *Bioorg Med Chem Lett.* 2001, 11, 2715-2717.
40. Curtis, D. R.; Hosli, L.; Johnston, G. A.; Johnston, I. H. *Exp Brain Res.* 1968, 5, 235-258.
41. Olsen, R. W.; Betz, H. In *Basic Neurochemistry: Molecular, Cellular and Medicinal Aspects*; G. J. Siegel, R. W. Albers, S. T. Brady and D. L. Price, Ed.; Academic Press: New York, N.Y., 2006; pp 291-301
42. Coyle, J. T. *Cell Mol Neurobiol.* 2006, 26, 365-384.
43. Javitt, D. C. *Biol Psychiatry.* 2008, 63, 6-8.
44. Phyllis, D. O. U.S. Pat. No. 3,083,229, 1963.
45. Li, M.; Johnson, M. E. *Synthetic Commun.* 1995, 25, 533-537.
46. Ratcliff, R.; Rodehors, R. *J Org Chem.* 1970, 35, 4000-&.
47. Brown, H. C.; Weissman, P. M.; Yoon, N. M. *J Am Chem Soc.* 1966, 88, 1458-&.
48. Cameron, D. W.; Feutrill, G. I.; Perlmutter, P. *Aust J Chem.* 1982, 35, 1469-1480.
49. Sethi, M. L. *J Pharm Biomed Anal.* 1993, 11, 613-617.
50. Sterni, S. H.; Fonnum, F. *Eur J Biochem.* 1978, 91, 215-222.
51. Lyles, G. A.; Callingham, B. A. *Biochem Pharmacol.* 1982, 31, 1417-1424.
52. Grant, S. L.; Shulman, Y.; Tibbo, P.; Hampson, D. R.; Baker, G. B. *J Chromatogr B Analyt Technol Biomed Life Sci.* 2006, 844, 278-282.

This background information is provided for the purpose of making known information believed by the applicant to be of possible relevance to the present invention. No admission is necessarily intended, nor should it be construed, that any of the preceding information constitutes prior art against the present invention.

All publications, patents and patent applications mentioned in this Specification are indicative of the level of skill of those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

We claim:
1. A compound having the formula (I), or a pharmaceutically acceptable salt thereof:

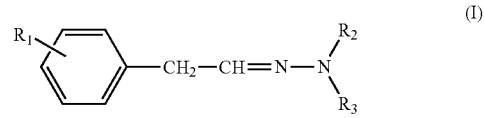

wherein $R_1$ is H, $R_2$ is $CH_2CCH$ and $R_3$ is $CH_2CCH$;
$R_1$ is H, $R_2$ is H and $R_3$ is $CH_2CCH$;
$R_1$ is $CH_3$, $R_2$ is H and $R_3$ is $CH_2CCH$;
$R_1$ is $OCH_3$, $R_2$ is H and $R_3$ is $CH_2CCH$;
$R_1$ is $C_1$, $R_2$ is H and $R_3$ is $CH_2CCH$;
$R_1$ is F, $R_2$ is H and $R_3$ is $CH_2CCH$;
$R_1$ is $CF_3$, $R_2$ is H and $R_3$ is $CH_2CCH$;
$R_1$ is $CH_3$, $R_2$ is $CH_2CCH$ and $R_3$ is $CH_2CCH$;
$R_1$ is $OCH_3$, $R_2$ is $CH_2CCH$ and $R_3$ is $CH_2CCH$;
$R_1$ is $C_1$, $R_2$ is $CH_2CCH$ and $R_3$ is $CH_2CCH$;
$R_1$ is F, $R_2$ is $CH_2CCH$ and $R_3$ is $CH_2CCH$; or
$R_1$ is $CF_3$, $R_2$ is $CH_2CCH$ and $R_3$ is $CH_2CCH$.
2. The compound of claim 1, wherein $R_1$ is H, $R_2$ is $CH_2CCH$ and $R_3$ is $CH_2CCH$.

3. The compound of claim 1, wherein $R_1$ is H, $R_2$ is H and $R_3$ is $CH_2CCH$.

4. A method of treating a subject suffering from schizophrenia comprising administering to said subject an effective amount of the compound of claim 1, a pharmaceutically acceptable salt thereof, or a pharmaceutically acceptable composition thereof.

5. The method of claim 4, wherein $R_1$ is H, $R_2$ is $CH_2CCH$ and $R_3$ is $CH_2CCH$.

6. The method of claim 4, wherein $R_1$ is H, $R_2$ is H and $R_3$ is $CH_2CCH$.

7. A method of increasing glycine levels in the brain of a subject comprising administering to said subject an effective amount of the compound of claim 1, a pharmaceutically acceptable salt thereof, or a pharmaceutically acceptable composition thereof.

8. The method of claim 7, wherein $R_1$ is H, $R_2$ is $CH_2CCH$, $R_3$ is $CH_2CCH$.

9. The method of claim 7, wherein $R_1$ is H, $R_2$ is H and $R_3$ is $CH_2CCH$.

10. A pharmaceutical composition comprising a therapeutically effective amount of the compound of claim 1 or a pharmaceutically acceptable salt thereof, and a pharmaceutically acceptable carrier.

11. The pharmaceutical composition of claim 10, wherein $R_1$ is H, $R_2$ is $CH_2CCH$, $R_3$ is $CH_2CCH$.

12. The pharmaceutical composition of claim 10, wherein $R_1$ is H, $R_2$ is H and $R_3$ is $CH_2CCH$.

13. A kit comprising:
   a. the compound of claim 1, or a pharmaceutically acceptable salt thereof; and
   b. instructions for the use thereof.

14. The kit of claim 13, wherein $R_1$ is H, $R_2$ is $CH_2CCH$, $R_3$ is $CH_2CCH$.

15. The kit of claim 13, wherein $R_1$ is H, $R_2$ is H and $R_3$ is $CH_2CCH$.

* * * * *

UNITED STATES PATENT AND TRADEMARK OFFICE
CERTIFICATE OF CORRECTION

PATENT NO.        : 8,501,995 B2                                         Page 1 of 1
APPLICATION NO.   : 12/833453
DATED             : August 6, 2013
INVENTOR(S)       : Glen Baker et al.

It is certified that error appears in the above-identified patent and that said Letters Patent is hereby corrected as shown below:

In the Claims

Column 20, line 58, delete "$C_1$" and insert therefor --Cl--.

Column 20, line 63, delete "$C_1$" and insert therefor --Cl--.

Signed and Sealed this
Twenty-fourth Day of December, 2013

Margaret A. Focarino
*Commissioner for Patents of the United States Patent and Trademark Office*